United States Patent
MacDonald et al.

(10) Patent No.: US 10,441,813 B2
(45) Date of Patent: Oct. 15, 2019

(54) METHOD AND SYSTEM FOR CANCER TREATMENT WITH RADIATION

(71) Applicant: DALHOUSIE UNIVERSITY, Halifax (CA)

(72) Inventors: R. Lee MacDonald, Halifax (CA); Christopher G. Thomas, Halifax (CA); James Leonard Robar, Halifax (CA)

(73) Assignee: DALHOUSIE UNIVERSITY, Halifax (CA)

( * ) Notice: Subject to any disclaimer, the term of this patent is extended or adjusted under 35 U.S.C. 154(b) by 483 days.

(21) Appl. No.: 15/320,659

(22) PCT Filed: Jul. 16, 2015

(86) PCT No.: PCT/CA2015/050664
§ 371 (c)(1),
(2) Date: Dec. 20, 2016

(87) PCT Pub. No.: WO2016/008052
PCT Pub. Date: Jan. 21, 2016

(65) Prior Publication Data
US 2017/0189717 A1     Jul. 6, 2017

Related U.S. Application Data

(60) Provisional application No. 62/025,402, filed on Jul. 16, 2014, provisional application No. 62/107,907, (Continued)

(51) Int. Cl.
*G06K 9/00* (2006.01)
*A61N 5/10* (2006.01)
(Continued)

(52) U.S. Cl.
CPC ............ *A61N 5/1039* (2013.01); *A61B 5/055* (2013.01); *A61B 6/032* (2013.01); *A61B 6/037* (2013.01);
(Continued)

(58) Field of Classification Search
None
See application file for complete search history.

(56) References Cited

U.S. PATENT DOCUMENTS 6,888,919 B2   5/2005   Graf
2002/0051513 A1*  5/2002  Pugachev ............. A61N 5/103
                                                          378/65
(Continued)

FOREIGN PATENT DOCUMENTS

JP    H0326242 A    2/1991
WO   2012024448 A3  2/2012

OTHER PUBLICATIONS

Das, Shiva K., and Lawrence B. Marks. "Selection of coplanar or noncoplanar beams using three-dimensional optimization based on maximum beam separation and minimized nontarget irradiation." International journal of radiation oncology, biology, physics 38.3 (1997): 643-655. (Year: 1997).*

(Continued)

*Primary Examiner* — Samah A Beg
(74) *Attorney, Agent, or Firm* — Tucker Ellis LLP

(57) ABSTRACT

Embodiments generally relate to cancer treatment with radiation sources. The present technology discloses techniques that can enable an automatic generation of radiotherapy trajectories using anatomical data of a patient. It can improve conformal dose distributions and target volume coverage by considering a radiation risk decided by an organs-at-risk (OAR)'s relative location to the target volume and the radiation source.

26 Claims, 23 Drawing Sheets

Related U.S. Application Data filed on Jan. 26, 2015, provisional application No. 62/160,308, filed on May 12, 2015.

(51) Int. Cl.
*A61B 6/03* (2006.01)
*A61B 5/055* (2006.01)
*A61B 6/00* (2006.01)
*G06F 19/00* (2018.01)

(52) U.S. Cl.
CPC .............. *A61B 6/504* (2013.01); *A61N 5/103* (2013.01); *A61N 5/1081* (2013.01); *A61N 5/1047* (2013.01); *G06F 19/3481* (2013.01)

(56) References Cited

U.S. PATENT DOCUMENTS

| | | | |
|---|---|---|---|
| 2005/0254622 A1* | 11/2005 | Llacer | A61N 5/1031 378/65 |
| 2011/0110491 A1* | 5/2011 | Vaitheeswaran | A61N 5/1042 378/65 |
| 2012/0035462 A1* | 2/2012 | Maurer, Jr. | A61B 6/5247 600/411 |
| 2017/0360932 A1* | 12/2017 | Parry | A61K 39/3955 |
| 2018/0078785 A1* | 3/2018 | Ollila | A61N 5/1036 |
| 2018/0078789 A1* | 3/2018 | Ollila | A61N 5/1039 |
| 2019/0030372 A1* | 1/2019 | MacDonald | A61N 5/103 |
| 2019/0054320 A1* | 2/2019 | Owens | A61N 5/1071 |

OTHER PUBLICATIONS

Cho, B. C. J., et al. "The development of target-eye-view maps for selection of coplanar or noncoplanar beams in conformal radiotherapy treatment planning." Medical Physics 26.11 (1999): 2367-2372. (Year: 1999).*

Bergner et al., Autoadaptive phase-correlated (AAPC) reconstruction for 4D CBCT, Med. Phys. vol. 36 No. 12 Dec. 2009, 5695-5706 pp. 12.

Oliver et al., A treatment planning study comparing whole breast radiation therapy against conformal, IMRT and tomotherapy for accelerated partial breast irradiation, Radiotherapy and Oncology vol. 82, 317-323, 2007,pp. 7 Canada.

Bentzen et al., Quantitative Analyses of Normal Tissue Effects in the Clinic (QUANTEC): An Introduction to the Scientific Issues, Int J Radiat Oncol Biol Phys, Mar. 1, 2010; 76(3 Suppl): S3-S9, pp. 11.

Lawrence et al., Radiation Dose—Volume Effects in the Brain, Int. J. Radiation Oncology Bioi Phys., vol. 76, No. 3, Supplement.pp. S20-S27, 2010 USA. pp. 8.

Yang et al., Choreographing couch and collimator in volumetric modulated arc therapy, Int. J. Radiation Oncology Biol. Phys., vol. 80 No. 4 pp. 1238-1247, 2011 USA, pp. 11.

International Search Report for PCT/CA2015/050664 dated Sep. 30, 2015, pp. 3.

Written Opinion of the International Searching Authority for PCT/CA2015/050664 dated Sep. 30, 2015; pp. 6.

* cited by examiner

| Arc Number | Field | Arc Length(°) | Table Rotation(°) | Collimator Angle(°) | Arc Direction | Start Angle (°) | Stop Angle (°) |
|---|---|---|---|---|---|---|---|
| 1 | 1 | 360 | 0 | 45 | CW | 181 | 179 |
| | 1 | 360 | 0 | 45 | CW | 181 | 179 |
| 2 | 2 | 180 | 315/45/90 | 45 | CCW | 179 | 359 |
| | 1 | 360 | 0 | 45 | CW | 181 | 179 |
| 3 | 2 | 180 | 315 | 45 | CCW | 179 | 359 |
| | 3 | 180 | 45 | 315 | CCW | 1 | 181 |
| 4 | 1 | 360 | 0 | 45 | CW | 181 | 179 |
| | 2 | 180 | 315 | 45 | CCW | 179 | 359 |
| | 3 | 180 | 45 | 315 | CCW | 1 | 181 |
| | 4 | 180 | 90 | 45 | CW | 181 | 1 |

*FIG. 10*

METHOD AND SYSTEM FOR CANCER TREATMENT WITH RADIATION

RELATED APPLICATIONS

This application claims priority to U.S. provisional application 62/025,402, filed Jul. 16, 2014, and entitled "Dynamic Couch Motion for Improvement of Radiation Therapy Trajectories," U.S. provisional application 62/107,907, filed Jan. 26, 2015, and entitled "Method and System for Cancer Treatment with Radiation," and U.S. provisional application 62/160,308, filed May 12, 2015, and entitled "Method and System for Cancer Treatment with Radiation," the disclosures of which are hereby incorporated herein by reference in its entirety for all purposes.

FIELD OF THE INVENTION

The disclosure relates generally to cancer treatment with radiation sources, and more specifically, to planning cancer treatment with a rotating radiation source.

BACKGROUND

Volumetric modulated arc therapy (VMAT) or arc therapy has been widely adopted in cancer radiotherapy. VMAT delivers radiation by rotating the gantry through one or more arcs. Compared with the conventional radiotherapy, VMAT can achieve highly conformal dose distributions with improved target volume coverage and cause less damage to normal tissues. Additionally, VMAT can reduce treatment delivery time compared with conventional radiotherapy, such as static field intensity modulated radiotherapy (IMRT).

SUMMARY

The present technology provides a method and system to generating a radiation trajectory treatment plan for VMAT or any arc-based radiation therapy technique. The present technology can generate a patient-specific treatment plan that can improve target volume coverage and reduce damage in healthy tissues.

Aspects of the present technology relate to techniques that enable dosimetric improvements by optimization of dynamic couch position or fixed-couch rotation position for cranial stereotactic treatments. This technology can also be feasibly applied in many extra-cranial sites of treatment.

According to some embodiments, the present technology discloses a non-transitory computer readable storage medium storing a computer program which when executed by at least one processor activates several functions and displays icons when each of a plurality of home screens is triggered, the computer program comprising sets of instructions for receiving anatomical imaging data of one or more organs-at-risk and a target volume, determining a two-dimensional, radiation-beam's-eye-view (BEV) centered on the target volume for each of a plurality of gantry positions; for each BEV for the plurality of gantry positions, calculating a foreground/background weighting factor, the foreground/background weighting factor indicating a risk of exposing a respective organ-at-risk within the BEV as a function of a relative depth within a patient of the respective organ-at-risk with respect to the target volume and the radiation source; and determining a preferred gantry position from the plurality of gantry positions by calculating a respective overlapping volume for the one or more organs-at-risk for each BEV for the plurality of gantry positions multiplied by the foreground/background weighting factor.

According to some embodiments, the present technology discloses a system for determining a trajectory of a radiation source in radiotherapy, comprising: a radiation source associated with a gantry angle, a patient support system associated with a patient support angle, one or more computer systems configured to: receive anatomical imaging data of one or more organs-at-risk and a target volume, determining a two-dimensional, radiation-beam's-eye-view (BEV) centered on a target volume for each of a plurality of gantry positions, calculate a foreground/background weighting factor for each BEV of the plurality of gantry positions, the foreground/background weighting indicating a risk of exposing a respective organ-at-risk within the BEV as a function of the relative depth within a patient of the organ-at-risk with respect to the target volume and the radiation source, calculate a respective overlapping volume for the each of the one or more organs-at-risk at each suitable gantry angle and each suitable patient support angle, modify the respective overlapping volume of the each of the one or more organs-at-risk based at least in part on the respective foreground/background weighting factor and a radiation sensitivity weighting factor associated with each of the one or more organs-at-risk, generate a geometric overlap map for the one or more organs-at-risk by summing the modified overlapping volume of the each of the one or more organs-at-risk, and generate a radiation trajectory using the geometric overlap map.

According to some embodiments, the present technology can calculate an urgent sparing factor for modifying the respective overlapping volume of the organ-at-risk when an organ-at-risk is within a predetermined distance to a target volume or receives a measure of excess dose. The urgent sparing factor is operable to reduce radiation exposure of the organ by selecting a radiation path such that the vector joining the OAR and PTV is substantially orthogonal to the BEV.

According to some embodiments, a radiation trajectory can comprise a range of gantry angles in correspondence to a range of patient support angles. According to some embodiments, a radiation trajectory can comprise a range of gantry angles suitable for a fixed patient support angles. Additionally, a radiation trajectory can comprise a range of patient support angles suitable for a fixed gantry angle.

According to some embodiments, the present technology can determine a maximum intensity projection based on anatomical imaging data of a group of patients, and generate a template geometrical map for the group of patients.

According to some embodiments, the present technology can compare a number of geometric overlap maps each being associated with a respective patient, and identify one or more similar anatomical characteristics to modify a patient's radiation trajectory based on these identified anatomical characteristics.

Using cranial stereotactic radiotherapy plans used at the Nova Scotia Cancer Centre (NSCC), a novel method for redesigning treatment arrangement is used to obtain the optimal couch rotation position based on the reduction of overlap score between organs-at-risk of exposure (OARs), and target volume (PTV). According to some embodiments, optimal trajectories can be created for dynamic simultaneous coordinated motion between couch positions and gantry positions. According to some embodiments, when the arc arrangement is determined for the delivered treatment, the couch position can be determined based on a cost function analysis of accumulation of overlap score from an existing equation. The algorithm incorporates factors for depth of both OAR and PTV volumes, and radiation dose sensitivities of each OAR.

The plan evaluation was conducted with the standard evaluation of cranial stereotactic radiotherapy plans at the NSCC. Maximum and mean doses to the OARs were reduced by approximately 35.48%±5.38% and 36.60%±4.68% (N=6) respectively with application of this optimization technique as compared to the delivered treatment plans. In addition, PTV coverage was maintained to the same degree as the delivered treatment.

This slight variation of the existing delivery techniques with guidance from a PTV-OAR overlap cost-function analysis technique can yield significant dosimetric improvements, with no increase to delivery or planning time.

Although many of the examples herein are described with reference to VMAT or arc therapy, it should be understood that these are only examples and the present technology is not limited in this regard. Rather, any external beam radiation therapy that can use radiation trajectories may be used, such as intensity modulated radiation therapy (IMRT) and image-guided radiation therapy (IGRT).

Additional features and advantages of the disclosure will be set forth in the description which follows, and, in part, will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

BRIEF DESCRIPTION OF THE DRAWINGS

Various embodiments or examples of the invention are disclosed in the following detailed description and the accompanying drawings:

FIG. 10 is an arc arrangement template disclosed by University of Alabama at Birmingham (UAB);

DETAILED DESCRIPTION

Figure 1:
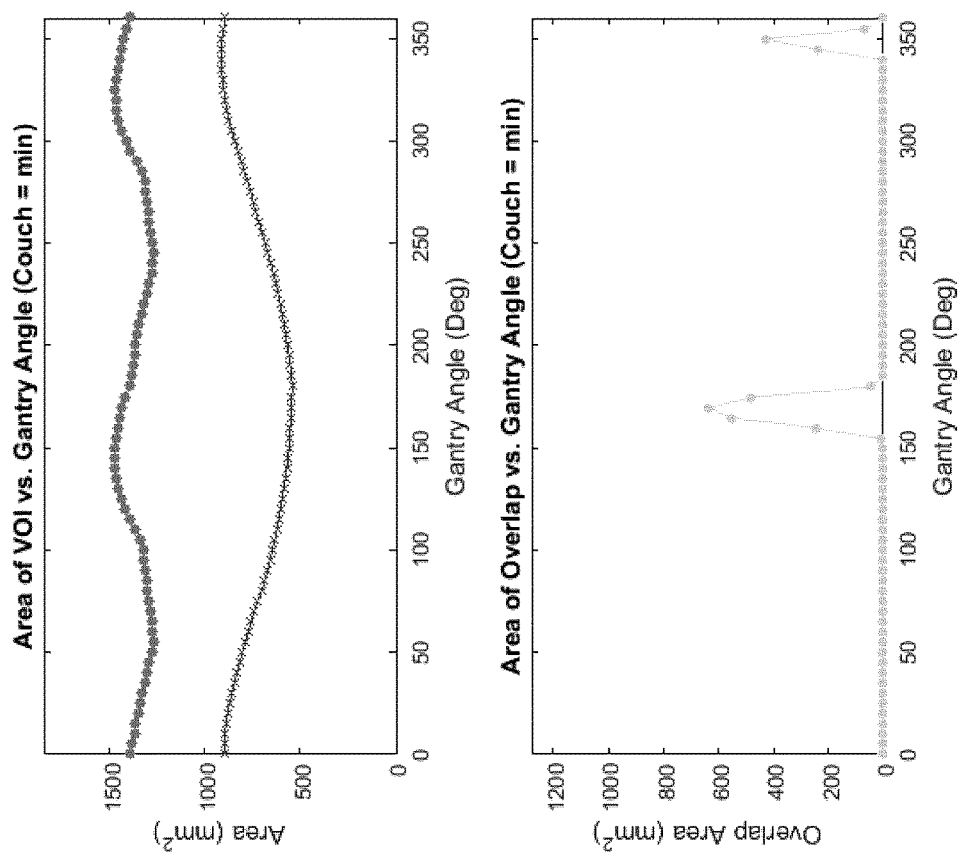
FIG. 1 displays the area projections of the PTV and an OAR and their corresponding overlap. In the first figure of FIG. 1, the area of the PTV is illustrated with circular markers and the area of the OAR illustrated with 'x' markers. In the second figure of FIG. 1, the overlap is illustrated with circular markers.

Various embodiments of the present technology are discussed in detail below. While specific implementations are discussed, it should be understood that this is done for illustration purposes only. A person skilled in the relevant art will recognize that other components and configurations may be used without departing from the spirit and scope of the present technology.

Cranial cancer plans are amongst the most complex and intricate cases to treat with radiation. The location and the size of the target volume can vary significantly within the cranial cavity, creating significant variations between cases. In addition, there are many critical organs surrounding the target, which are very sensitive to exposure to radiation. The location of the target volume can be very close to these sensitive structures, causing them to receive high doses of radiation during the curative treatment. Significant radiation exposure to these volumes can cause permanent loss of function in vital organs of the cranial region. Technology designed to diminish the risk of exposure to sensitive healthy volumes surrounding the target is a high priority in all radiotherapy modalities. This works aims to further refine cranial stereotactic radiation therapy techniques by modifying the points of entry of radiation to the body to reduce any doses to sensitive structures.

Dynamic Couch Motion for Improvement of Radiation Therapy Trajectories

Aspects of the present technology dependent on the anatomical information of a test-patient for calculation of the quantity of overlap present at every couch-gantry (CG) coordinate. As this research aims to create a general approach to permit the assessment of any patient, it needs to comply with the current procedural work flow to be feasible to implement in the treatment planning process. This procedure can be a non-invasive step in the planning process which uses existing and readily-available information without disturbance of the current treatment planning arrangement. From the time the radiotherapy patient arrives at the hospital for the first time until delivery, there is a well-established planning process to which this research seeks to be a potential addition. As such, it utilizes the same initial information as the treatment planner to make decisions based on ensuring the delivery of the prescription dose to the target while limiting the dose to normal tissue.

Importing Anatomical Information

The patient's anatomical information is taken from the computed tomography (CT) images from the patient's initial CT scan. This is the vital source of information for patient treatment planning as it is a representation of the internal anatomy of the patient. These CT slices are transverse cross-sections of the patient taken at equal spacing across the portion of the patient relevant for treatment. These cross sections allow treatment planners to see into the patient and examine the arrangement of internal structures. To identify these structures, the outline of the shape of the structure is drawn, or contoured, in each CT slice in which it is present. These two-dimensional contours are then interpolated between each slice in which they are drawn to create a three-dimensional structure showing the outline of the volume. This effectively gives the treatment planner the ability to clearly visualize the outline of all important volumes within the patient anatomy.

This patient anatomical information can be exported from Eclipse (Varian Medical Systems, Inc., Palo Alto, USA), the treatment planning software at the Nova Scotia Cancer Centre (NSCC), in a series of DICOM-format files. These files contain CT slices and the contouring information designed by the treatment planner. These DICOM files also contain reference points which allow the treatment planner to design and align the treatment according to known locations within the treatment delivery room, as well as all the treatment planning beams. Using the information in the file containing the contoured structures, projections of these three-dimensional contoured volumes can be calculated after importing them into MATLAB (The MathWorks, Inc., Natick, Mass., U.S.A.).

Calculation of Overlap

As the gantry position changes, the X-ray source position is altered with respect to the patient. This means that the radiation beam's path has now been modified to approach the patient on a new incident trajectory. This creates a new configuration for the anatomical structures within the patient as seen from the X-ray source and requires a new assessment of what is between the source and the treatment target at each new position. We are also changing the orientation of the patient support system (patient treatment couch), which also rotates the anatomy of the patient about the coronal axis of the rotation at the treatment system isocentre.

As we are trying to assess the amount of overlapping sensitive organs-at-risk (OAR) with our target volume (PTV) as seen from the X-ray source, it is important to accurately model the changes made to the arrangement of the anatomical structures as we alter the orientation of the patient with respect to the source. To assess the overlap between two structures, we project their three-dimensional structures onto a two-dimensional plane. This plane is located at the machine isocentre, a fixed location within the treatment planning room, which is a static defining feature of radiotherapy planning. Projecting structures accurately to a two dimensional plane generates what is equivalent to the radiation beam's eye view (BEV). This is defined as the view from within the aperture of the gantry's primary radiation beam as seen from the X-ray source. The position of the gantry and the patient couch alters the constituents of the BEV and the arrangement of the anatomy. Each unique BEV will correspond to different values of overlap for each OAR and target (PTV).

Since the DICOM structure file contains the information we need regarding the relative positioning of the three-dimensional volumes contoured, we can extract from this the arrangement of the patient. The desired OAR for comparison is chosen from a list of volumes and each volume is projected onto a two-dimensional isocentric plane with the PTV by drawing a line from the source position, based on the rotational position of the gantry, through each point that makes up the volume. This effectively draws the structure as it would be viewed from the source position and each point is a representation of a projection line drawn from the source, through the volume, onto the plane at isocentre.

Mutual Plotting Method

The two-dimensional coordinate points that compose each of the structures (OAR and PTV) being evaluated are drawn and the coordinates are filed into an xy-coordinate system based on the vertical and horizontal location of the points on the plane. The code simultaneously projects multiple volumes onto the same plane, inside of the same visualization window in MATLAB. This visualization window can remain at a suitable size to contain both volumes during their full rotation in both the plane of the couch rotation and the plane of the gantry rotation.

The angles over which the code is being analyzed are input by the user for both the rotation of the couch, and the rotation of the gantry, along with the interval at which each are being iterated. Along with these, the PTV and OAR indices and the isocentre location are extracted from the DICOM file and input into the projection program in order to accurately represent the structures with reference to a central point of rotation (the isocentre). A coordinate space is established and defined in which the plane viewed from the X-ray source position is the xz-plane and a rotation in the y-direction indicates a patient support system rotation. The intial vectors for the xz-plane are found for a gantry and couch angle of zero and the source location is established 100.0 cm away in the y-direction (for gantry and couch angle zero). Rotational matrices are then established for both couch and gantry rotations in order to properly apply these rotations to the xz-plane. The three-dimensional rotation matrix for the couch is a rotation about the y-axis given as:

$$\begin{pmatrix} \cos\theta_C & 0 & \sin\theta_C \\ 0 & 1 & 0 \\ -\sin\theta_C & 0 & \cos\theta_C \end{pmatrix}$$

where $\theta_C$ is the current value for the couch rotation. The rotation of the gantry is a rotation about the z-axis, which can be represented by the three-dimensional rotation matrix as:

$$\begin{pmatrix} \cos\theta_G & -\sin\theta_G & 0 \\ \sin\theta_G & \cos\theta_G & 0 \\ 0 & 0 & 1 \end{pmatrix}$$

where $\theta_G$ is the current value for the gantry rotation. These rotations are then applied to the source position, and the initial vectors which establish the plane are also adjusted to represent the structures as currently visible between source and new isocentric plane. This process is iterated from first to final gantry angle and from first to final couch angle at their respective specified intervals.

At each couch and gantry rotation (CG) coordinate position, the coordinates of the structures which have been reduced to their two-dimensional projections are each drawn and a profile is drawn around the exterior of each. The area of the profile of each the structure is drawn using the convhull MATLAB function, which returns the 2D convex hull of the projection areas. This area is measured and registered using the trapz MATLAB function for trapezoidal numeric integration. This area is filed according to the current CG-position for later calculation.

The two-dimensional coordinates that constitute a projected volume are then adjusted to adhere to a fixed grid. This grid is established to find similarly drawn points between both structures, which are utilized as coordinates corresponding to a volume representing the geometric overlap between the two structures. When each structure currently being registered for overlap is plotted, the coordinate points, which constitute the area in which these overlap, are not always aligned. This means that if a coordinate is tested within an overlapping area of one of the structures to see if it is present in the other structure, while the two may be very close, the points will not mutually be found. However, if we correct these points to adhere strictly to a two-dimensional grid, the points which are in close proximity in both volumes can be correctly established as mutual. The grid spacing which was most accurate was empirically established of having a spacing of 0.32 mm², and this was determined by using two spheres of known areas of projection with a known area of overlap between the two.

All points within one volume are tested to see if they can be found mutually in both volumes. The points that do have mutual points in each volume are understood to be overlapping coordinates and are filed according to their index within the evaluated structure. These points are then registered based on their location before the adjustment to the grid had occurred. While the grid has only marginally adjusted them, the true location of these points was as they were drawn initially in the structure. These points represent the overlap area between the two volumes, using the coordinates of one of the evaluated structures. This overlap area then undergoes the same assessment as the two initial volumes for establishing the area of the plotted coordinates by using the convex hull (convhull function) and trapezoidal numerical integration (trapz function) procedures.

Generation of Overlap Scoring Map: Geometric Overlap Score Equation and Map

The previous section describes the method for calculating the overlap found between a PTV and a single chosen OAR at a specific couch/gantry positioning. This process is conducted iteratively for every CG-coordinate that is a valid combination of couch and gantry positioning for treatment.

FIG. 1 displays the area projections of the PTV and an OAR and their corresponding overlap. In the first figure of FIG. 1, the area of the PTV is illustrated with circular markers and the area of the OAR illustrated with "x" markers. In the second figure of FIG. 1, the overlap is illustrated with circular markers.

The evaluation proceeds with the couch in a fixed position and the gantry is allowed to rotate in a full rotation as specified by the user. The result is a set of overlap calculation values for all the gantry positions at this specific couch angle. The first figure of FIG. 1 shows the plotting of this data for an evaluation of two volumes: a PTV shown in the circular markers and the spinal cord shown in the "x" markers. The second figure of FIG. 1 shows the values for the overlap between the two structures at a fixed couch position while the gantry is rotated in a full 360° rotation. The largest peak, which is centred at approximately 120°, is the BEV in which the spinal cord is between the source and the PTV and a large area of the spinal cord overlaps with that of the PTV, a foreground overlap. The second slightly smaller peak, which centres at approximately 295°, corresponds to the OAR being in a background overlap in which the PTV is between the OAR and the source. These overlap scenarios do not correspond to equivalent risk and are not equivalently compared, as the scenario in which the OAR must be traversed in order to deliver sufficient dose to the PTV is a much less desirable arrangement for radiotherapy treatment, which is explained in details in the following specification.

The ranking of every valid gantry and patient support combination is conducted via a method proposed by Yang et al. ([1] Yang et al. "Choreographing Couch and Collimator in Volumetric Modulated Arc Therapy." International Journal of Radiation Oncology, Biology, Physics 80, no. 4 (Jul. 15, 2011): 1238-47. doi:10.1016/j.ijrobp.2010.10.016.) Yang et al. evaluates the amount of geometric overlap between the radiotherapy PTV and every OAR of radiation exposure within the patient anatomy. This overlap, E(c,g), is evaluated for each gantry (g) and patient support rotational angle (c) via Equation 1, where $w_i$ is a relative weighting factor for the $i^{th}$ OAR, $L_i(c, g)$ is the overlap area between the PTV and the $i^{th}$ OAR, $A_i(c, g)$ is the area of the ith OAR, and $A_t(c,g)$ is the area of the PTV. These areas are based on the projections of the PTV and OARs onto a plane as defined at the distance of the rotational axis of the gantry from the radiation source position.

$$E(c, g) = \sum_i w_i \times \left[ \frac{L_i(c, g)}{A_t(c, g)} \times \frac{L_i(c, g)}{A_i(c, g)} \right][1] \qquad (1)$$

In order to analyze the entire couch/gantry space, these measurements can be taken at each couch angle in addition to every gantry angle.

Once we have a measurement such as that shown in the second figure of FIG. 1, we file this information along the ordinate (gantry angle) for a specified couch angle $\theta_C$, which is specified on the abscissa. The amplitudes of the values are indicated via a map in which the high-density shading indicates the most overlap present and the low-density shading indicates the least amount of overlap. (See FIG. 2 for an example of a completely mapped CG-coordinate overlap space for one OAR.)

Figure 2:
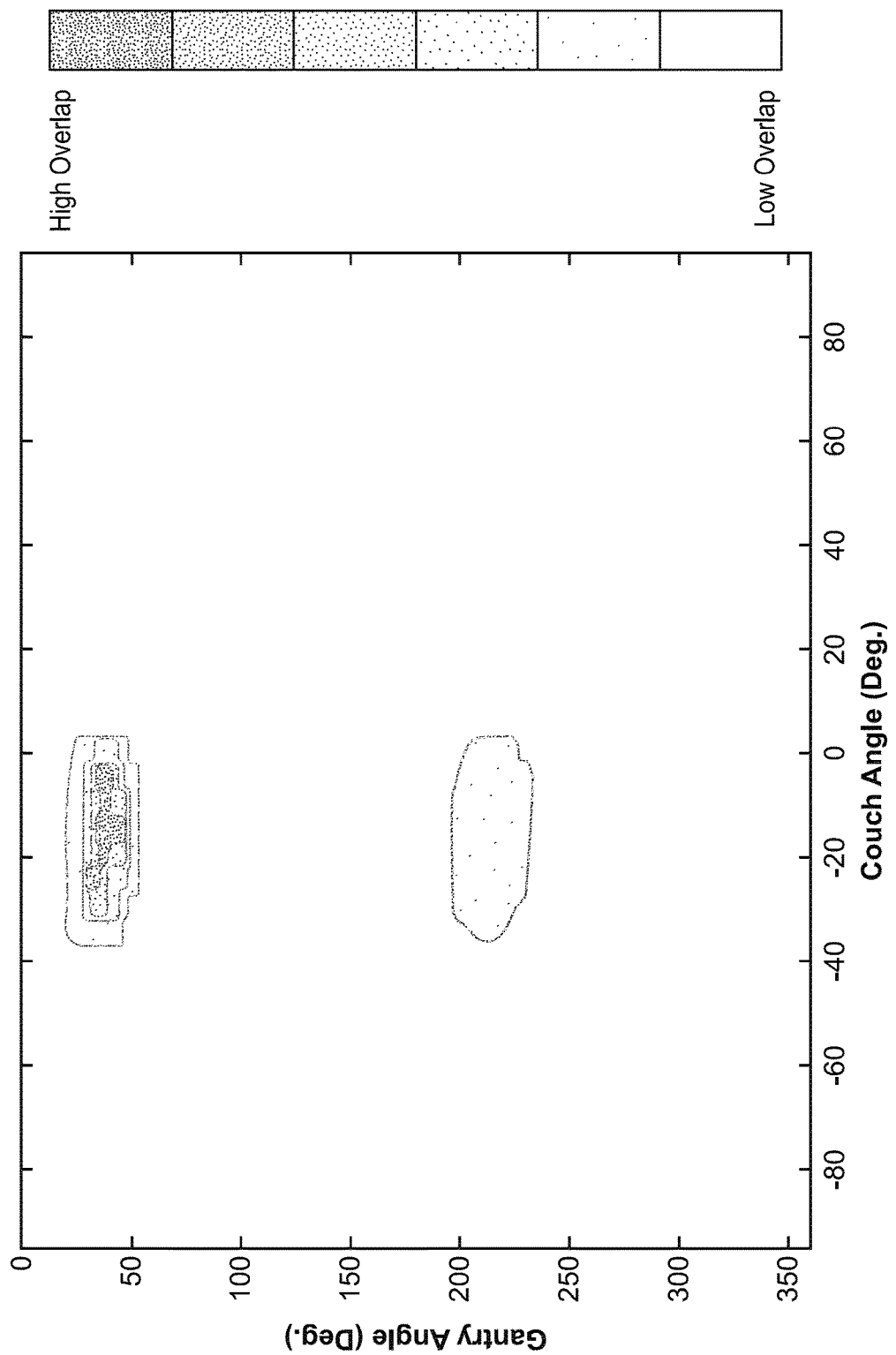
FIG. 2 illustrates an overlap map between the PTV and the left eye.

FIG. 2 illustrates an overlap map between the PTV and the left eye.

We have introduced a new foreground/background weighting factor, F, to Equation 1 in order to account for the possibility that the overlap can occur in the space between the PTV and the source (a foreground overlap), or can occur behind the PTV (a background overlap). This is a coefficient that minimizes the overlap value by a factor of ten in the case of a background overlap. Equation 1 with the foreground/background factor F is Equation 2:

$$E(c, g) = \sum_i w_i \times F \times \left[ \frac{L_i(c, g)}{A_t(c, g)} \times \frac{L_i(c, g)}{A_i(c, g)} \right] \quad (2)$$

Another additional weighting factor is radiation sensitivity weighting factor $w_i$, which relates the importance of these OARs relative to one another. All exposure to organs cannot be evaluated equivalently as all OARs cannot tolerate the same quantity of dose. As such, the overlap of these OARs can be weighted to according to this sensitivity.

One of the clinical references for the sensitivity of an organ-at-risk is the Quantitative Analysis of Normal Tissue Effects in the Clinic (QUANTEC) ([2] Y. R. Lawerence, X. A. Li, I. el Naqa, C. A. Hahn, L. B. Marks, T. E. Merchant, and A. P. Dicker, "Radiation dose-volume effects in the brain," International Journal of Radiation Oncology*Biology*Physics 76, no. 3 (Mar. 1, 2010)). With the assistance of QUANTEC, the algorithm can appropriately incorporate a heirarchial system to rank the OARs according to their need for limiting the exposure to radiation dose. Additionally, Hall et al ([3] Hall, Eric J., and Amato J. Giaccia. Radiobiology for the Radiologist. Lippincott Williams & Wilkins, 2006) was consulted for clinical radiation dose constraints. If the constraining value found in Hall was more conservative than that found in QUANTEC, the value from Hall was used. The radiation dose limitations to these organs given by QUANTEC [2] and Hall et al [3] are listed in Table 1. The radiation sensitivity weighting factor $w_i$ is the organ weighting factor which we have defined as the inverse dose constraints given by QUANTEC or Hall et al [3]:

$$w_i = \frac{1}{D_{tol}},$$

where $D_{tol}$ is the tolerance limit in Gy for that particular OAR. Exceeding the tolerance limit for an OAR results in an increased probability of toxicities or complications in that OAR. This tolerance limit can either be a maximum dose to any part of the organ or a mean dose, depending on the OAR in question. The overlap score for an individual pixel is thus more expansively represented as:

$$E(c, g) = \sum_i \frac{1}{D_{tol_i}} \times F \times \left[ \frac{L_i(c, g)}{A_t(c, g)} \times \frac{L_i(c, g)}{A_i(c, g)} \right] \quad (3)$$

While there is variability among anatomical positioning throughout the cranial cases analyzed, the surrounding OAR are common throughout the patients. A cranial cancer case is very proximal to the ocular structures, such as the eyes, optic chiasm, optical nerves, optical tracts, and lenses, as well as the brainstem and healthy brain tissues.

The weighting factors $w_i$ and F will further modify the geometric overlap map for each OAR. Once a weighted geometric overlap map for each OAR has been calculated, all maps are summed to produce a total geometric overlap map for all OARs.

TABLE 1

Dose limitations for the most common OARs in cranial cancer cases.

| Organ at risk of exposure | Dose Constraint (Gy) | Limit Definition | Risk of Exceeding | Reference |
| --- | --- | --- | --- | --- |
| Brainstem | 54 | Maximum dose (<5% Rate) | Cranial Neuropathy or Necrosis | QUANTEC |
| Chiasm | 55 | Maximum dose (<3% Rate) | Optic Neuropathy | QUANTEC |
| Lens | 10 | Maximum dose (TD 5/5) | Cataract | Hall |
| Eye | 45 | Maximum dose (TD 5/5) | Blindness | Hall |
| Optic Nerve | 55 | Maximum dose (<3% Rate) | Optic Neuropathy | QUANTEC |
| Optic Tract | 55 | Maxium dose (<3% Rate) | Optic Neuropathy | QUANTEC |
| Normal Brain | 45 | Maximum (TD 5/5) | Infarction, necrosis | Hall |
| Cochlea | 45 | Mean dose (<30% Rate) | Hearing Loss | QUANTEC |
| Pituitary | 45 | Maximum (TD 5/5) | Hypopituitarism | Hall |

Generation of Overlap Scoring Map: Collision Zones

Due to the physical configuration of the gantry and patient support system, there are certain CG-coordinates which are not valid for entry in the geometric overlap map. These values account for the positioning of the gantry and couch in which the two occupy the same space inside the treatment room. If these CG-coordinates were included in the trajectory and delivered to the machine for treatment, the gantry and couch would collide in attempting to reach these positions. These positions are aptly named collision zones. These collision zones also include regions in which the gantry would collide with the space that the patient would occupy.

These collision zones were experimentally measured on a Varian TrueBeam STx (Varian Medical Systems, Inc., Palo Alto, USA) Linear Accelerator (TB2) at the NSCC. An anthropomorphic phantom was positioned in a typical treatment arrangement for cranial cancer patients. The treatment couch was positioned at a longitudinal position of 90.85 cm, a vertical position of 15.00 cm, and a lateral position of 0.00 cm. The couch was positioned at the one extreme of its rotation travel and moved in one degree increments across its total range. A point in a collision zone was recorded for which the couch position and gantry position were such that: (i) the collision avoidance system of the TrueBeam was triggered, or (ii) the gantry was within a 5 cm buffer to either the treatment bed or the anthropomorphic phantom. The CG-coordinates within these zones were assigned a value higher than the normalized maximum of whatever value was measured for overlap within a map in order that a coordinate within a collision zone could never be included in the optimized trajectory (see FIG. 3 for an example).

Figure 3:
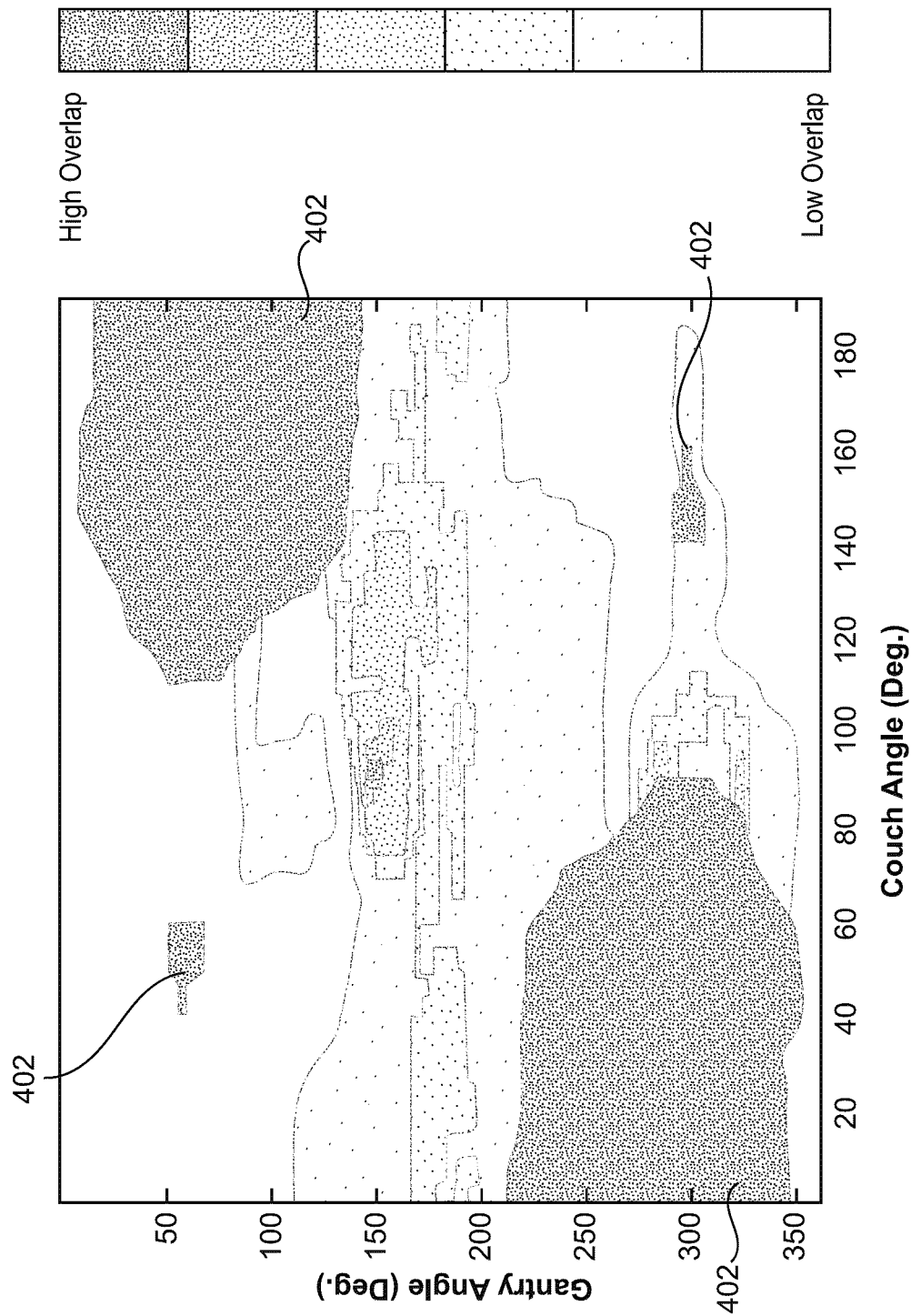
FIG. 3 illustrates an overlap map with all OARs for the patient included. The high-density shading regions indicate collision zones of the CG space.

FIG. 3 illustrates an overlap map with all OARs for the patient included. The high-density shading regions indicate collision zones (e.g., 402) of the CG space.

Algorithm for Trajectory Navigation

Figure 4:
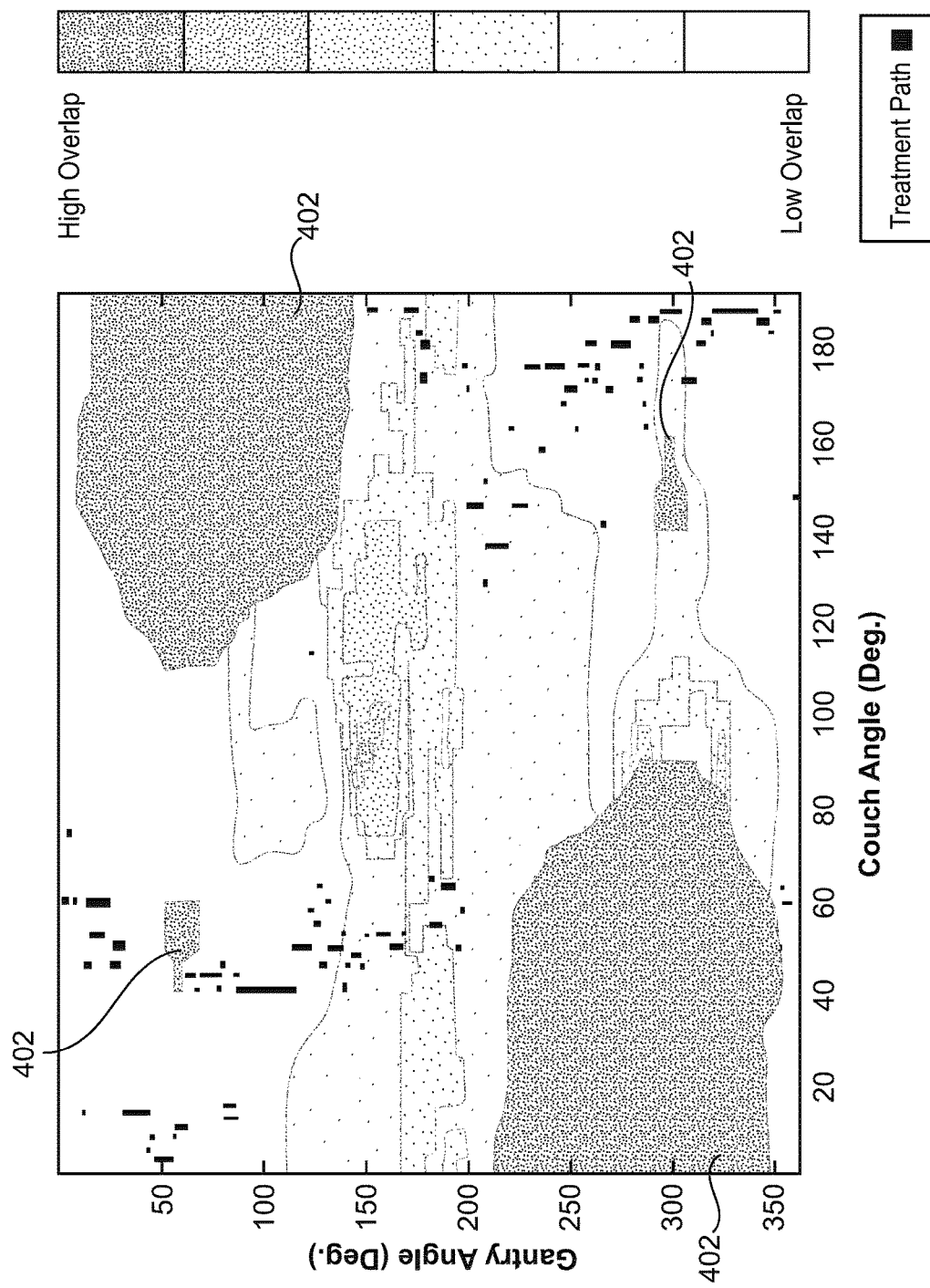
FIG. 4 illustrates an overlay of the trajectory or treatment path, indicated as straight lines, designed by identifying the patient support and gantry positions that correspond to the minimum output from Equation 3.

The weighted overlap map is used by the trajectory design algorithm, which then determines a navigable path through this overlap map in the most effective and efficient means possible. The first step in this process is identifying, for each independent gantry angle, the patient support angle that has the lowest value of $E(c,g)$ from Equation 3. For each gantry angle, these coordinates are indications of the position the patient support system ought to be in to achieve the lowest possible amount of overlap. Radiation delivery at these coordinates would be the trajectory that corresponds to the least amount of radiation exposure to OARs by the primary radiation beam. However, the trajectory output by identifying the minimum values from Equation 3 (example as shown in FIG. 4) is not useful clinically due to the extreme discontinuity of the patient support motion. There are far too many discrete movements in couch and gantry positioning to be realistic. The algorithm can now seek to create a smooth patient support trajectory, which will increase delivery time, while simultaneously working to minimize the values of the overlap within the optimized trajectory.

FIG. 4 illustrates an overlay of the trajectory or treatment plan, indicated as straight lines, designed by identifying the patient support and gantry positions that correspond to the minimum output from Equation 3. FIG. 4 includes multiple collision zones 402.

Parameter Entry for Smoothing

Any patient support position that is an absolute minimum for a particular gantry position is a desirable component for building the treatment trajectory. Any other patient support position used would have a higher overlap value and would be a less desirable coordinate to include in the trajectory. The ability to use these absolute minimums depends on the absolute minimums at nearby gantry positions. If these minimums can be delivered without patient support motion or with minimal motion to connect these points, they are suitable for use in the trajectory.

Figure 5:
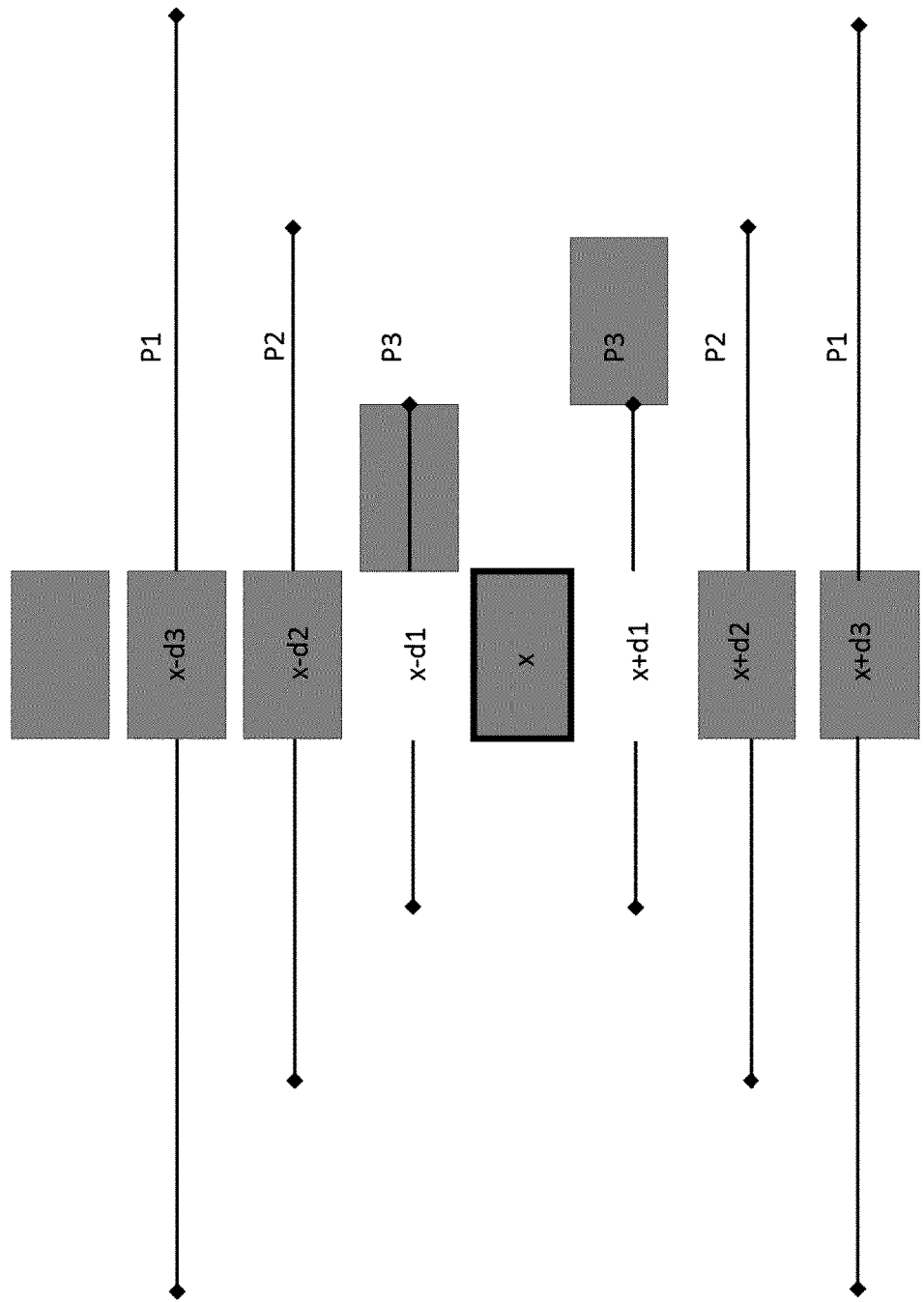
FIG. 5 illustrates a visualization of the flexible threshold evaluation of the patient support position for suitability in the trajectory.

The evaluation of the suitability of absolute minimum coordinates can be conducted using an originally designed threshold method which examines the stability of existing nearby coordinates. At three customizable gantry positions ahead and behind of the evaluated gantry coordinate (d3, d2, d1), customizable parameters are established (P1, P2, P3), as depicted in FIG. 5. At each of these locations, the parameters are used as a threshold to search if any desirable patient support system positions are within a reasonable distance from the evaluated point. According to the number of desirable nearby coordinates that fall within these parameters ahead and behind of the evaluated point, a ranking is established as an indication of how suitable this absolute coordinate point would be for inclusion in a treatment trajectory. The higher the number of desirable points, the higher the ranking. The user can then select the limit for the minimum score on this evaluation they will accept for inclusion in their optimized trajectory.

FIG. 5 illustrates a visualization of the flexible threshold evaluation of the patient support position for suitability in the trajectory.

The optimized trajectory now includes only absolute minimum positions which have been evaluated above a certain value of suitability for inclusion in the trajectory. All other points which fall below this value contribute to the discontinuity of the initially constructed trajectory and are discarded. The result is a number of short sub-arcs, as displayed in the example shown in FIG. 6. The next step is to connect these sub-arcs in a smooth path while maintaining minimal overlap of OARs within the trajectory. The gantry positions which have yet to have assigned patient support positions in the trajectory can be temporarily filled in by simply joining the end-points of the existing sub-arcs previously established. This is conducted by simple interpolation, which smoothly fills in the gaps between these sub-arcs to complete the trajectory.

Figure 6:
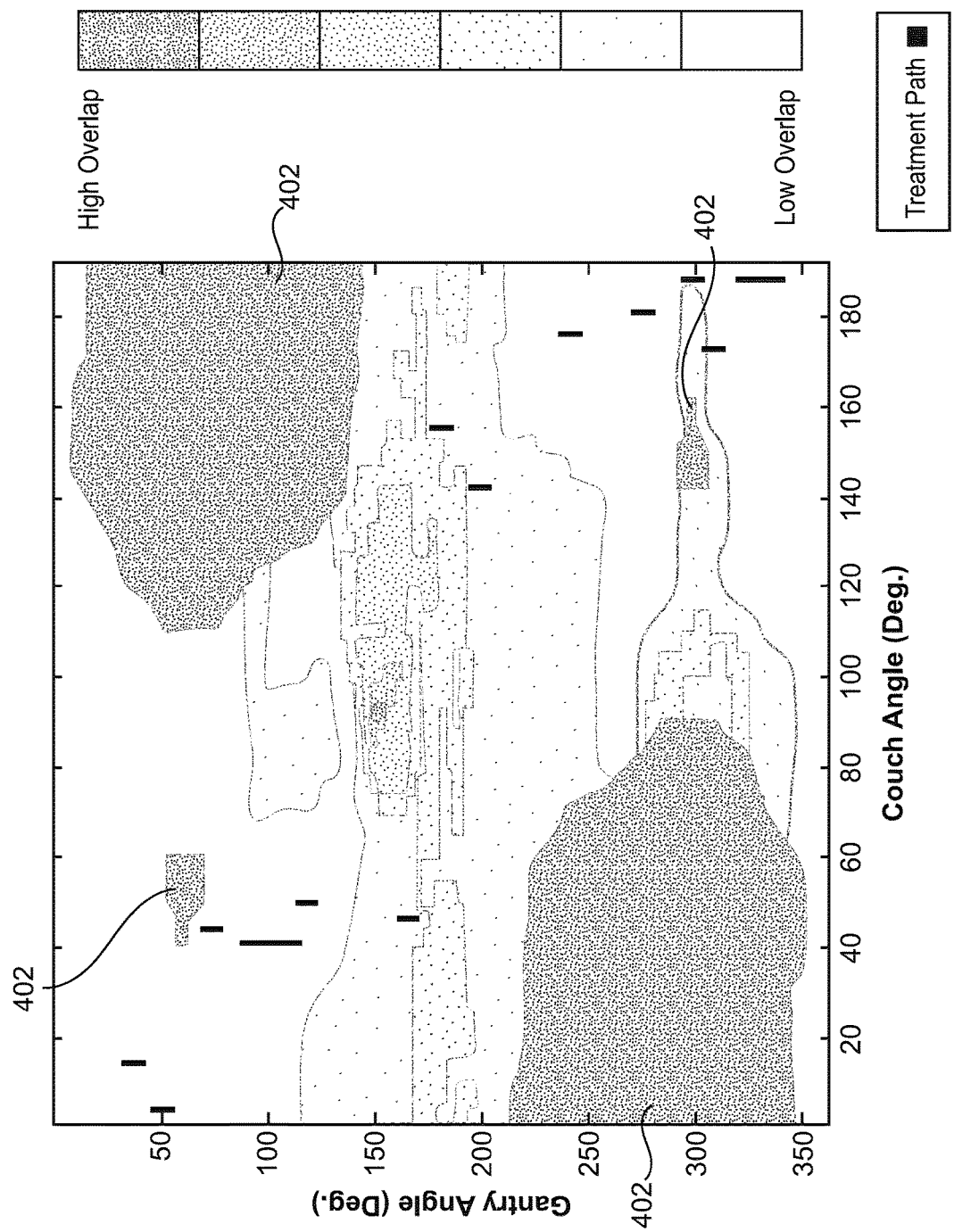
FIG. 6 illustrates an example of the trajectory or treatment path, indicated as straight lines, after the absolute minimum coordinates have been reduced to include only positions within the user-specified evaluation criteria.

FIG. 6 illustrates an example of the trajectory or treatment path, indicated as straight lines, after the absolute minimum coordinates have been reduced to include only positions within the user-specified evaluation criteria. FIG. 5 includes multiple collision zones 402.

As previously stated, the objectives for the algorithm are two-fold: to ensure the smooth and quick delivery of the treatment, and minimize the overlap throughout the trajectory. This simple interpolation is in line with the former, but it does not take into account the minimization of overlap. An additional evaluation is conducted on each point within the interpolation to ensure that these portions of the trajectory do not contribute to significant addition of overlap. At each interpolated point, the algorithm examines the nearby patient support positions at a customizable distance k away from the existing point for a smaller value of overlap (see FIG. 7). If a patient support position within the specified distance away has a smaller overlap value, the algorithm will change the patient support coordinate to this value. A complete trajectory is displayed in FIG. 8.

Figure 7:
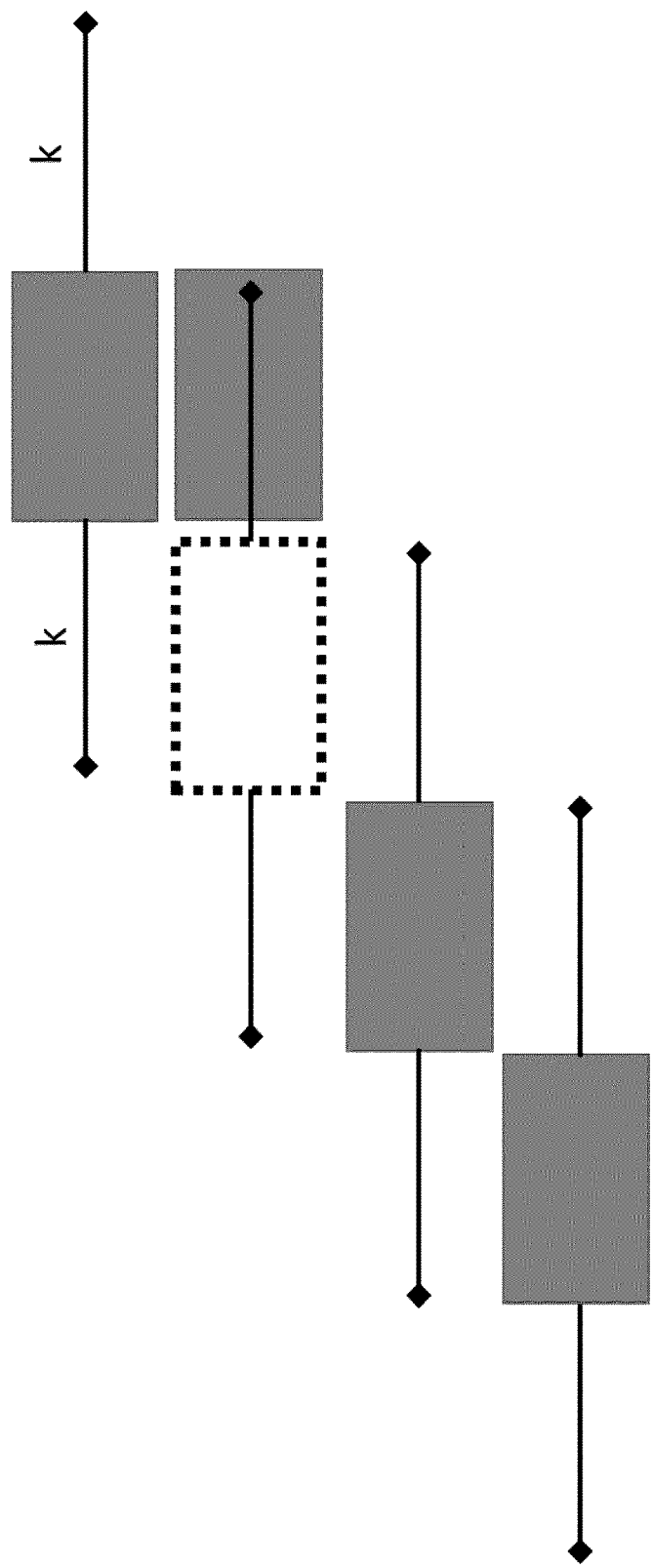
FIG. 7 illustrates visualization of the evaluation of nearby patient support positions with an improved overlap value for interpolated gantry coordinates. The dashed rectangle represents a former interpolated point. The point to its right is an adjusted coordinate.

FIG. 7 illustrates visualization of the evaluation of nearby patient support positions with an improved overlap value for interpolated gantry coordinates. The dashed rectangle represents a former interpolated point. The point to its right is an adjusted coordinate.

Figure 8:
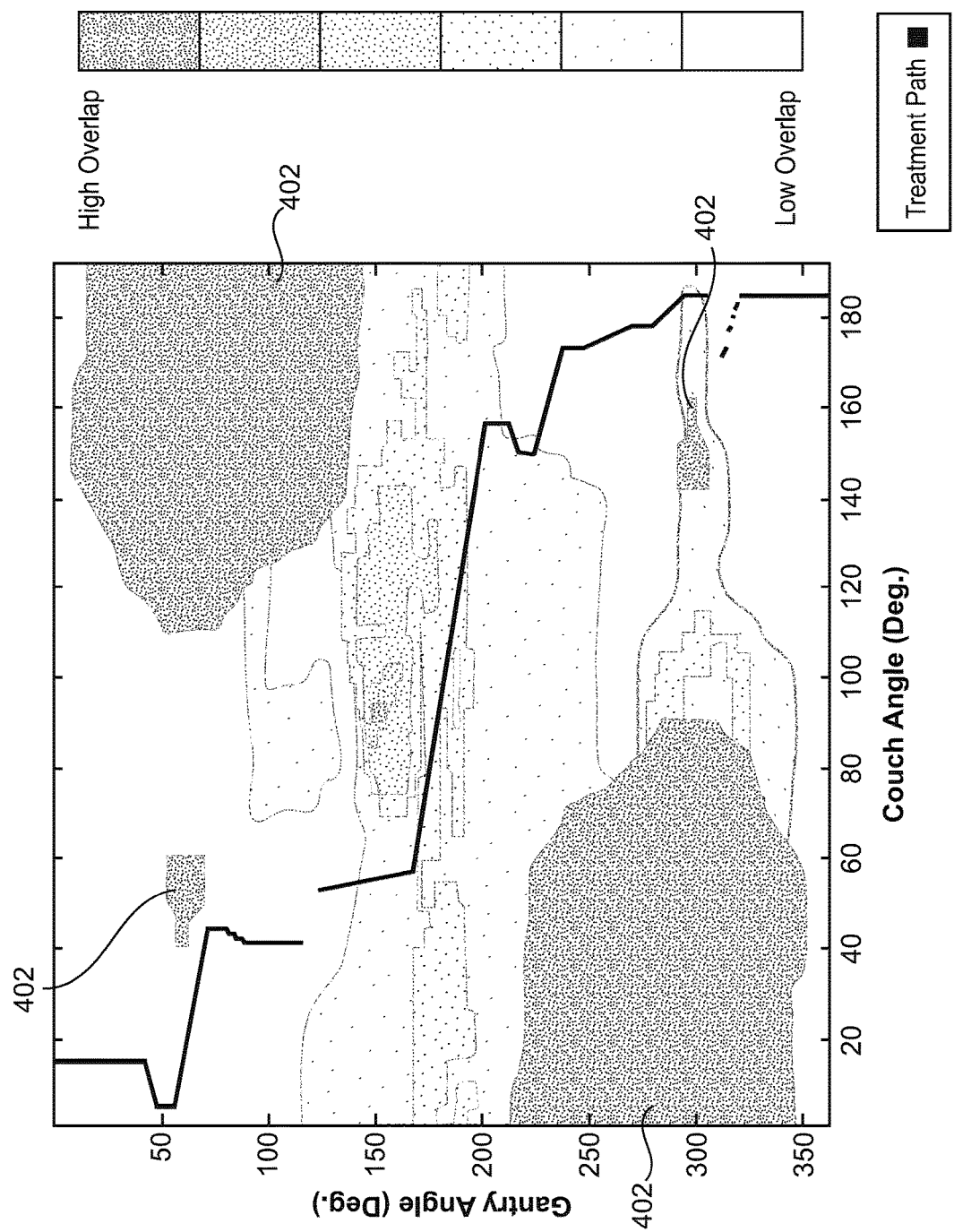
FIG. 8 illustrates an example of a completed treatment trajectory, indicated as straight lines, overlaying the patient-specific overlap map.

FIG. 8 illustrates an example of a completed treatment trajectory, indicated as straight lines, overlaying the patient-specific overlap map. FIG. 8 includes multiple collision zones 402.

Output Parameters

As output, the algorithm displays:

Patient specific weighted geometric overlap map of all OARs.

A visualization of all the absolute minimum coordinates.

A visualization of the minimum coordinates included in the optimized trajectory.

An overlay of the final optimized trajectory with the geometric overlap map.

In addition, a matrix is created which includes the final coordinates of an optimized trajectory.

As additional output parameters, the algorithm also provides:

Percentage of absolute minimum coordinates used in the final optimized trajectory.

Percentage of accumulated overlap score that the smoothing process contributes to trajectory overlap.

Percentage of accumulated overlap score of a treatment with patient support at a 0° position for an entire 360° gantry rotation, i.e.—no patient support motion for the same patient.

The approximate time added to move the patient support system to all locations within the trajectory.

All of these output parameters and display windows allow the user to make a judgment on whether the final output trajectory designed by the input parameters meets the specific needs and priorities of the intended optimization. The algorithm can be iterated repeatedly while altering any of the input thresholds or parameters until the user's trajectory is appropriate.

Restrictions for Import into Eclipse

The output of the trajectory design algorithm is a dynamic trajectory involving simultaneous couch and gantry motion for a full gantry rotation of 360°. This trajectory is optimized according to user-specified priorities regarding overlap between the OARs and the PTV, the treatment delivery time, and the scale of the couch motions. This trajectory can be imported to a treatment planning system capable of performing dose modulation and collimation adjustments for a radiotherapy trajectory containing simultaneous couch and gantry rotation.

Unfortunately, Eclipse has a number of restrictions that will not allow the fully optimized trajectory to be input for VMAT optimization, including not supporting simultaneous gantry and couch motion. To overcome the restriction of simultaneous motion in order to be accepted by the VMAT optimization algorithm, the optimized trajectory can be divided into subsections, which take any couch motion and divide it into discrete subarcs of gantry motion containing fixed couch kicks. At the extreme, a plan could be broken into 360 subarc fields of length one degree of gantry motion (individual control points) and combined to be a single plan. However, this division of the trajectory into sub-fields runs into further restrictions set by the VMAT optimization algorithm in the version of Eclipse (v.11) currently available at the NSCC. The restrictions are: the plan cannot contain more than ten arcs, and the arcs cannot be 30° or shorter of gantry motion. The trajectory output by the algorithm can thus be additionally simplified to comply with these restrictions in order to be VMAT optimized.

The simplified trajectory can be a plan which features ten arcs (the maximum accepted by the algorithm), eight of which are of gantry length 30.1° (with a 0.1° overlap in the range of gantry motion between these arcs) and two of which can be 60° (to complete the 360° gantry motion). The couch position of each one of these arcs is selected by summing all the overlap values over the length of one arc at each couch position and then selecting the minimum total value over the possible couch positions. The new trajectory is a radiotherapy plan with ten arcs containing ten separate couch-kicks which have been selected based on the weighted overlap map generated by Equation 3. These plans represent the highest degree of granularity possible for use within the VMAT optimization algorithm. See FIG. 9 for an example of such a trajectory.

Figure 9:
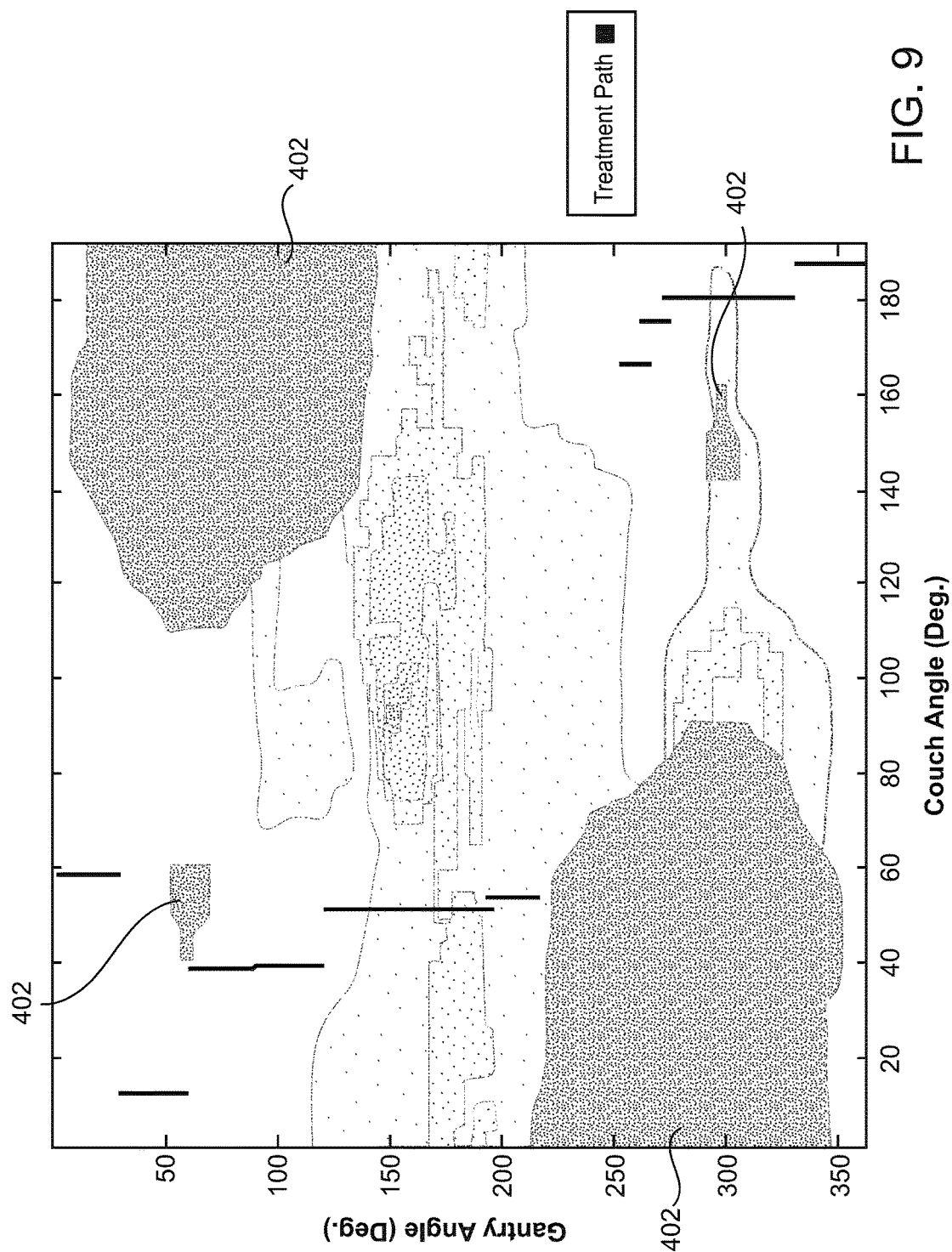
FIG. 9 illustrates simplified trajectory indicated as straight lines, with the maximum couch motion able to comply with the Eclipse restrictions on VMAT Optimization.

FIG. 9 illustrates simplified trajectory indicated as straight lines, with the maximum couch motion able to comply with the Eclipse restrictions on VMAT Optimization. FIG. 9 includes multiple collision zones 402.

Comparison of Conventional Trajectory to Optimized Trajectory

The technique is being applied to cranial cancer cases due to proximity of critical structures to the target volume. Also, the location of the isocentre near the end of the patient support system allows for maximum range of motion for both the support couch and the gantry. The criteria for inclusion as a test patient in this study are cranial cases with more than a single fraction, in other words stereotactic radiotherapy (SRT) patients.

Once a clinical case has been identified, that patient's CT set, plan, and structure set are exported, anonymized using DicomCleaner (PixelMed Publishing) software, and then re-imported into Eclipse as a test patient.

The test patient is given an ID number corresponding to the sequence in which they have been analyzed. The anonymized radiation therapy plan DICOM file (RTPlan.dcm) and contoured structure information (RTStruct.dcm) are imported to MATLAB. The PTV is chosen from the list of contoured structures. An iterative loop is then run which analyzes the PTV and each of the OARs in the structure file and generates an overlap map similar to that seen in FIG. 2. Each of these overlap maps is then fitted with the collision zones as measured for the cranial treatment position. The overlap maps for each OAR are then weighted according to the corresponding dose constraint from Table 1, weighted also with the F-factor, and combined to form a total weighted overlap map for all of the OARs. The total overlap map is then used to determine the ten subarcs (eight of 30.1°, two of 60° of gantry motion) each with unique couch positions that cover a total of 360° gantry rotation with the least amount of overlap. This corresponds to the maximum amount of motion allowed for a plan to still be valid for acceptance by the Eclipse VMAT optimization algorithm.

The customized plan is then imported to the test patient in Eclipse, along with the conventional previously delivered clinical plan. The conventional treatment plan is unaltered and the dose objectives that have been used to design the conventional plan are then used for the VMAT optimization of the optimized trajectory. The VMAT optimization is applied in three iterations. For each OAR, maximum and mean dose for both the conventional and customized trajectories are compared. PTV coverage for both plans is set such that the 90% isodose curves cover 99.5% of the PTV volume. The homogeneity and conformity of the PTV are then compared between the conventional and optimized trajectories.

Fixed Couch Position for Improvement of Radiation Therapy Trajectories

Aspects of the present technology provide for planning of a cranial stereotactic radiotherapy (SRT) treatment with a fixed-couch approach, which means that for each individual gantry arc, the patient treatment couch is positioned once. A radiotherapy arc is a subset of the treatment in which the gantry performs a dynamic rotation around the patient, delivering radiation along a path between the radiation source and the radiotherapy target (PTV). A radiotherapy trajectory is defined as the motion of all moving components of the radiation delivery system throughout an arc, in our case, the gantry and couch rotations. Cranial SRT at the NSCC utilizes a template technique developed by the University of Alabama at Birmingham (UAB).

Three to four arcs are used in a plan, and for each of these arcs, the couch is positioned 45° apart, with one arc at the 0° position. These arc lengths and couch positions are applied to all patients, regardless of PTV size and location. In some of these cranial SRT cases, the PTV is in very close proximity to vital organs-at-risk of exposure (OARs). The trajectories defined in the template receive no modification as a result of this proximity and possibility of increased dose to the OARs.

FIG. 10 illustrates an arc arrangement template disclosed by University of Alabama at Birmingham (UAB).

Figure 11:
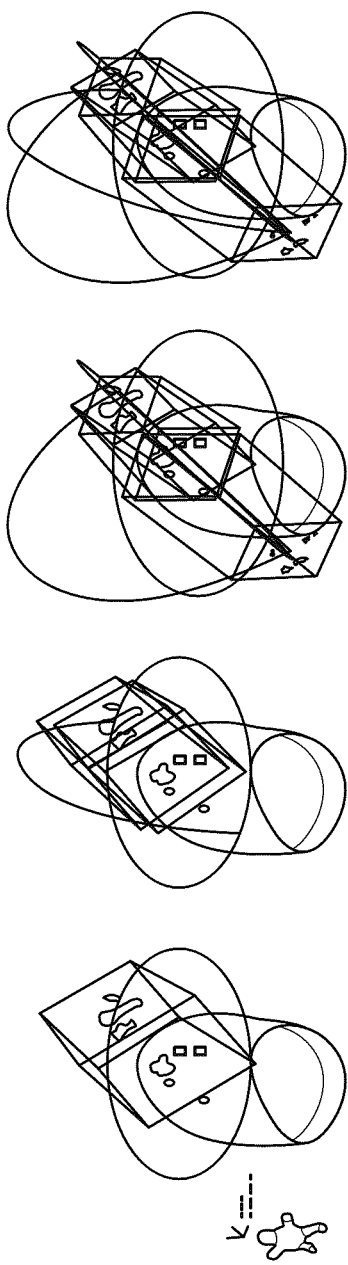
FIG. 11 illustrates four trajectory paths with reference to the cranial cavity, according to some embodiments. From right to left, 1 arc, 2 arc, 3 arc, and 4 arc arrangements are respectively shown (based on FIG. 10)

FIG. 11 illustrates four trajectory paths from the UAB template with reference to the cranial cavity, according to some embodiments. From right to left, 1 arc, 2 arc, 3 arc, and 4 arc arrangements are respectively shown.

This research aims to guide the definition of the couch rotation angles for a multi-arc plan based on the quantity of overlap present in the arc from the OAR-PTV geometric overlap score (GOS) map. This approach modifies the quantity of overlap between the OARs and PTV present in the trajectory and thus diminishes the amount of risk inherent in the treatment plan.

Method:

The position of the gantry and the patient couch alters the constituents of the radiation beam's-eye-view (BEV) and the arrangement of the anatomy with respect to it; consequently, each unique BEV will correspond to different values of overlap for each OAR and PTV.

For each gantry and couch coordinate, both the PTV and OAR were projected onto a two-dimensional isocentric plane by drawing a line from the source position, based on the rotational position of the gantry and couch, through each point that makes up the volumes. This draws the structures on a plane as viewed from the radiation source.

The user can supply the angles for both the rotation of the couch and the rotation of the gantry to the computer software, along with the interval at which each was being iterated. A coordinate space was defined in which the plane viewed from the X-ray source position is the xz-plane. The initial vectors for the xz-plane were found for a gantry and couch angle of zero and the source to isocentric plan distance were 100.0 cm in the y-direction. Rotational matrices were applied to the xz-plane for both couch and gantry rotations. The three-dimensional rotation matrix for the couch was a rotation about the y-axis given as:

$$\begin{pmatrix} \cos\theta_C & 0 & \sin\theta_C \\ 0 & 1 & 0 \\ -\sin\theta_C & 0 & \cos\theta_C \end{pmatrix}$$

where $\theta_C$ is the current value for the couch rotation. The rotation of the gantry was a rotation about the z-axis, which can be represented by the three-dimensional rotation matrix as:

$$\begin{pmatrix} \cos\theta_G & -\sin\theta_G & 0 \\ \sin\theta_G & \cos\theta_G & 0 \\ 0 & 0 & 1 \end{pmatrix}$$

where $\theta_G$ is the current value for the gantry rotation. This process was iterated from first to final gantry angle and from first to final couch angle at their respective specified intervals.

For each couch and gantry angle combination, all points within one projected structure were tested to see if they could be found mutually in both projected structures. The points that did have mutual points in each projected structure were understood to be overlapping coordinates and were filed according to their index within the evaluated structure and represent the overlap area between the two structures.

The ranking of every gantry and patient support combination was conducted via a method proposed by Yang et al ([1].), which evaluates the amount of geometric overlap between the PTV and every OAR and classifies a large amount of overlap as a high ranking. Using the nomenclature established by Yang et al [1], this overlap, E(c,g), was evaluated for each gantry (g) and patient support rotational angle (c), where $w_i$ is a relative weighting factor for the $i^{th}$ OAR, $L_i(c, g)$ is the overlap area between the PTV and the $i^{th}$ OAR, $A_i(c, g)$ is the area of the $i^{th}$ OAR, and $A_t(c,g)$ is the area of the PTV (see Equation 4). These areas are based on the projections of the PTV and OARs onto a plane as defined at the isocentre. The normalization to the projection area of the PTV and OAR compensates for variations in sizes of these volumes. Once we have an overlap measurement, this information was filed in a couch-gantry (CG) space, where gantry angle ($\theta_G$) was along the ordinate and couch angle ($\theta_C$) was along the abscissa. This is defined as the geometric overlap space (GOS). The amplitudes of the values are indicated via a map, as in the example shown in FIG. 13.

All patients included in this study had a treatment that was designed using a 6MV photon beam. The percent dose deposition (PDD) curve of this beam in water has a distinct shape and curve unique to this energy spectrum. This curve can be used as a reference to approximate the level of dose given to tissue at an equivalent depth in water.

When the target volume and the sensitive organ overlap, there are two distinct possible scenarios: the first, that the OAR is between the source of radiation and the PTV, and the second, that the PTV is between the source of radiation and the OAR. These scenarios pose different risks to the OAR and thus need to be weighted differently. In the first case, the radiation has to first traverse the OAR in order to reach the PTV, meaning more exposure to this OAR. This is a "foreground" overlap because the OAR is in the foreground. A "background" overlap still poses a risk for the OAR, however since it is found at a larger depth, the radiation does not expose it to the same degree. The foreground/background weighting factor (F) is an additional factor, which provides further insight to the conditions of the patient anatomical arrangement, and is based on the relative depth in the patient of each OAR ($d_1$) and PTV ($d_2$). By taking the PDD value of each object (PTV and OAR), and measuring the ratio of these, we have a more accurate calculation of the decrease/increase in risk due to background/foreground overlap scenarios (see FIG. 12).

Figure 12:
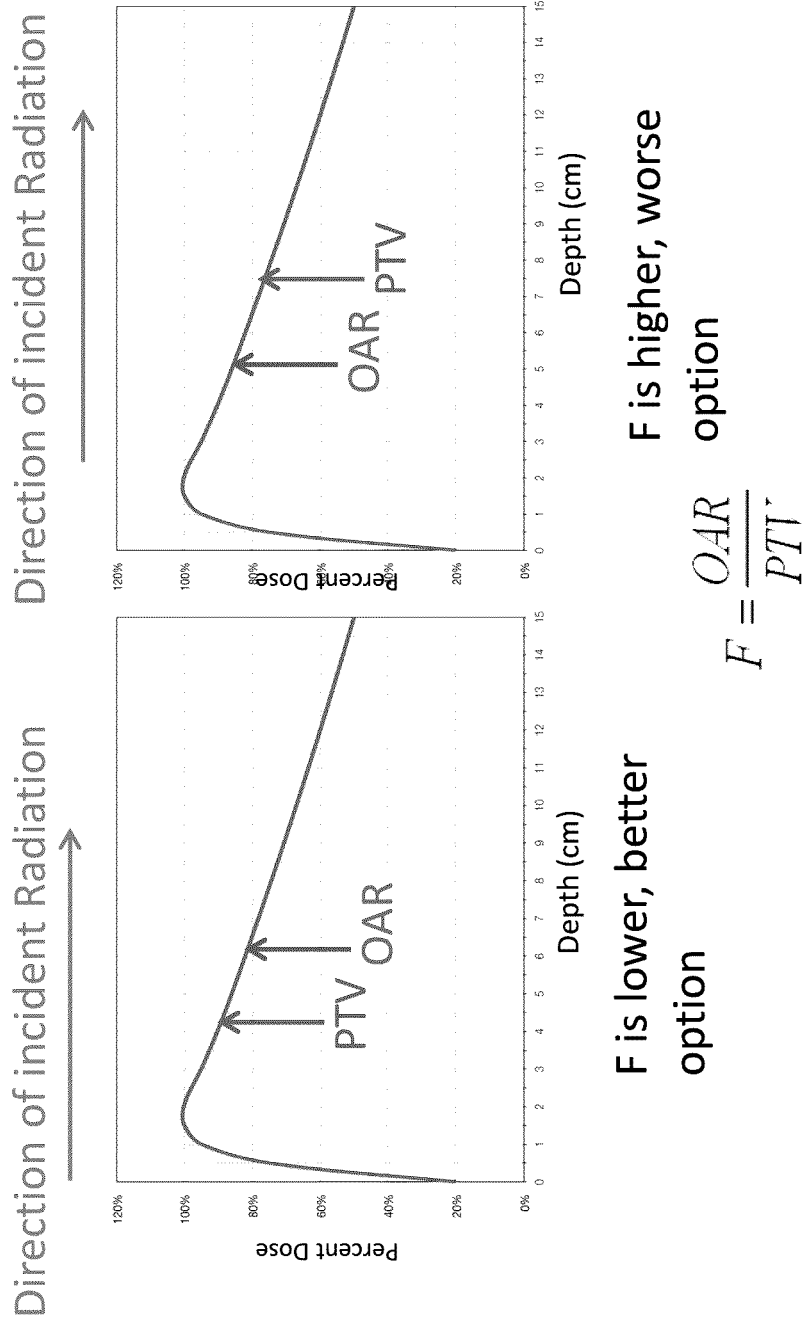
FIG. 12 shows schematic plot of the two scenarios and the locations of the PDD values as shown on the 6MV PDD curve, according to some embodiments.

FIG. 12 shows schematic plots of the two scenarios and the locations of the PDD values as shown on the 6MV PDD curve, according to some embodiments.

Figure 13:
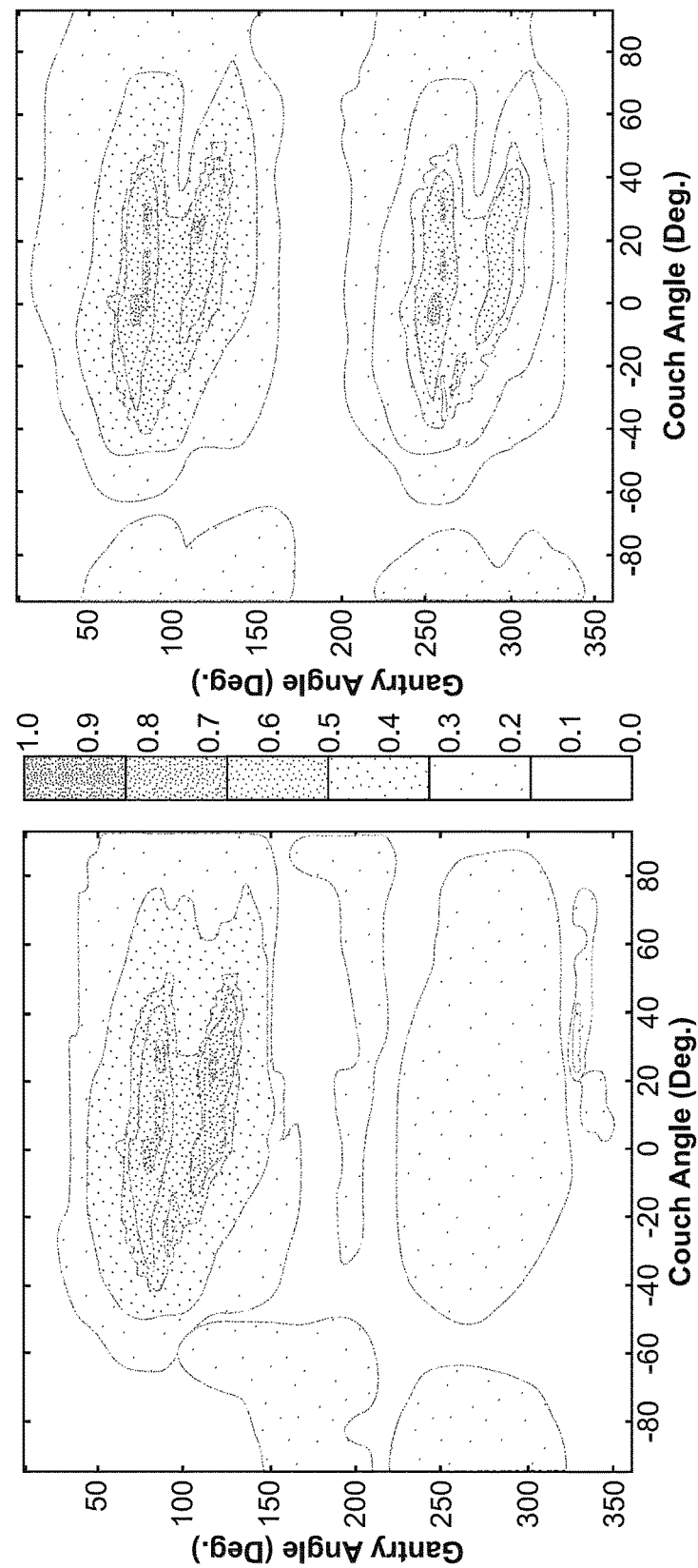
FIG. 13 illustrates: Left—The overlap map between the brainstem and the PTV with the arbitrarily established 10% foreground reduction that had previously been used [1]; Right—The overlap map between the brainstem and PTV with the PDD defined foreground/background weighting factor F included.

By incorporating this newly revised factor, the overlap maps for each individual OAR can be significantly modified to weight each scenario according to the risk associated with an OAR being in the foreground or background. FIG. 13 shows the changes in the overlap map that result from incorporation of the revised F-factor into the weighting equation (Equation 4). The resulting improvements from incorporating the newly revised F-factor, can be seen in FIG. 14 for a typical patient.

FIG. 13 illustrates: a) the first figure illustrates the overlap map between the brainstem and the PTV with the arbitrarily established 10% foreground reduction; b) the second figure illustrates the overlap map between the brainstem and PTV with the PDD-defined foreground/background weighting factor F-factor included.

Figure 14:
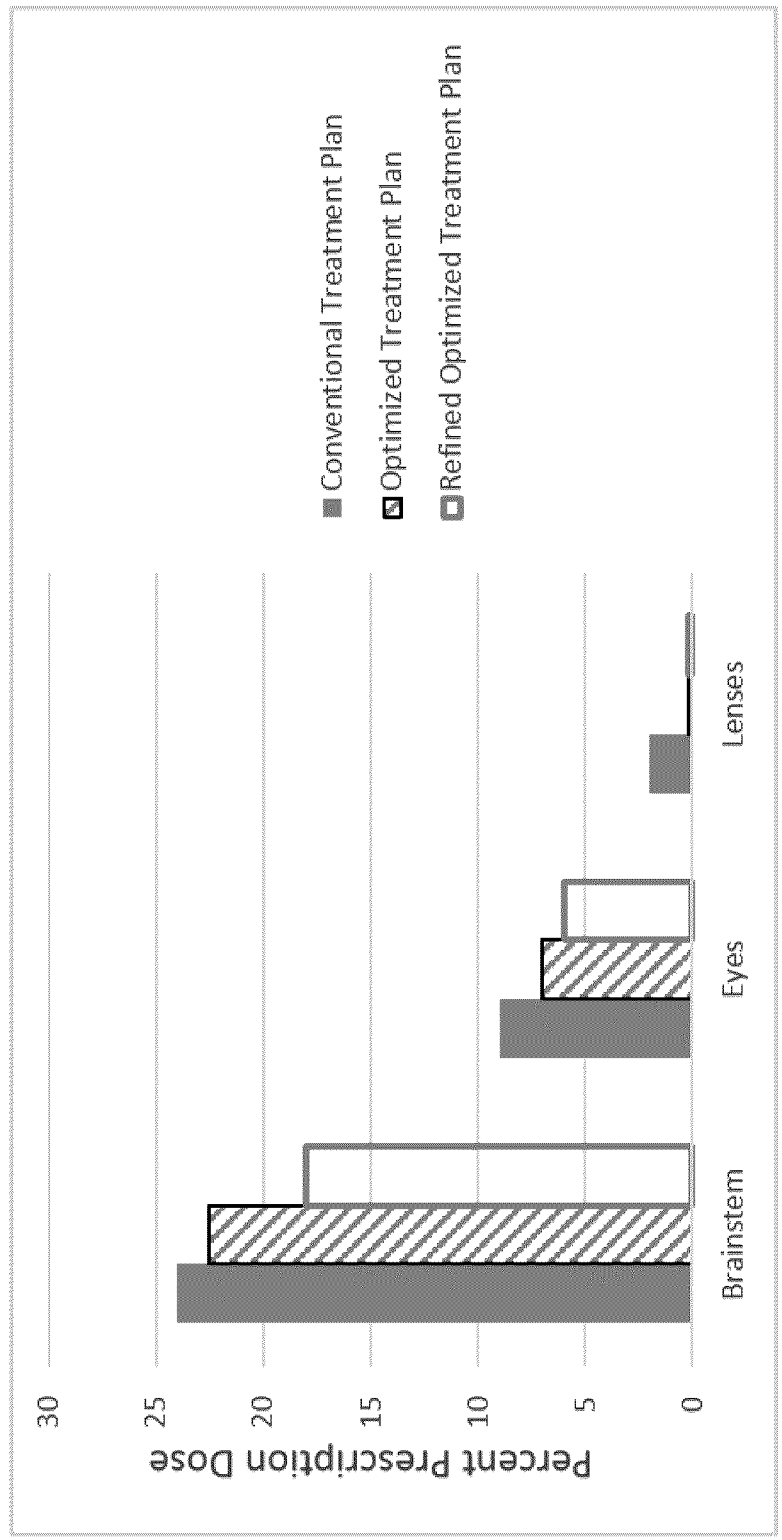
FIG. 14 shows conventional plans previously delivered compared with the results of optimization of these plans according to provisional patent Application No. 62/025,402, and results of the inclusion of the improved foreground overlap factor.

FIG. 14 shows conventional plans previously delivered compared with the results of optimization of these plans according to provisional patent Application No. 62/025,402, and results of the inclusion of the improved foreground overlap factor. This process was performed individually for each patient in the study.

In addition, we have defined the radiation sensitivity weighting factor $w_i$ as relating the importance of these OARs relative to one another. All exposure to organs cannot be evaluated equivalently as all OARs cannot tolerate the same quantity of dose. As such, the overlap of these OARs was weighted according to this sensitivity and was based on dose constraints given by Quantitative Analysis of Normal Tissue Effects in the Clinic (QUANTEC) ([4] Bentzen, Soren M., Louis S. Constine, Joseph O. Deasy, Avi Eisbruch, Andrew Jackson, Lawrence B. Marks, Ten Haken, Randall K, and Ellen D. Yorke. "Quantitative Analyses of Normal Tissue Effects in the Clinic (QUANTEC): An Introduction to the Scientific Issues." International Journal of Radiation Oncology Biology Physics 76, no. 3 (Mar. 1, 2010)) and Hall et al ([5] Hall, Eric J., and Amato J. Giaccia. Radiobiology for the Radiologist. Lippincott Williams & Wilkins, 2006). If the constraining value found in Hall et al was more conservative than that found in QUANTEC, the value from Hall et al was used. The radiation dose limitations, $D_{tol}$, to these organs given by QUANTEC and Hall et al are listed in Table 2. We define $w_i$ as $$\frac{1}{D_{tol_i}},$$

where $D_{tol_i}$ is me tolerance limit in Gy for the $i^{th}$ OAR. This would result in units of $Gy^{-1}$ for E(c,g), which we chose to ignore in the final construction of GOS. The overlap score for an individual coordinate is thus more expansively represented as:

$$E(c, g) = \sum_i w_i \times F(d1, d2) \times \left[\frac{L_i(c, g)}{A_t(c, g)} \times \frac{L_i(c, g)}{A_i(c, g)}\right] \quad (4)$$

$$= \sum_i \frac{1}{D_{tol_i}} \times \frac{PDD(d_1)}{PDD(d_2)} \times \left[\frac{L_i(c, g)}{A_t(c, g)} \times \frac{L_i(c, g)}{A_i(c, g)}\right]$$

where $d_1$ is the depth of the OAR and $d_2$ is the depth of the PTV.

TABLE 2

Dose limitations for the most common OARs in cranial cancer cases.

| Organ at risk of exposure | Dose Constraint (Gy) | Limit Definition | Risk of Exceeding | Reference |
|---|---|---|---|---|
| Brainstem | 54 | Maximum dose (<5% Rate) | Cranial Neuropathy or Necrosis | QUANTEC [4] |
| Chiasm | 55 | Maximum dose (<3% Rate) | Optic Neuropathy | QUANTEC [4] |
| Lens | 10 | Maximum dose (TD 5/5) | Cataract | Hall et al [5] |
| Eye | 45 | Maximum dose (TD 5/5) | Blindness | Hall et al [5] |
| Optic Nerve | 55 | Maximum dose (<3% Rate) | Optic Neuropathy | QUANTEC [4] |
| Optic Tract | 55 | Maximum dose (<3% Rate) | Optic Neuropathy | QUANTEC [4] |
| Normal Brain | 45 | Maximum dose (TD 5/5) | Infarction, necrosis | Hall et al [5] |
| Cochlea | 45 | Mean dose (<30% Rate) | Hearing Loss | QUANTEC [4] |
| Pituitary | 45 | Maximum (TD 5/5) | Hypopituitarism | Hall et al [5] |

Due to the physical configuration of the gantry and couch, there were certain CG-coordinates which were not valid for entry in the geometric overlap map due to possible collision between the gantry and couch or patient. These collision zones were measured on a Varian TrueBeam STx (Varian Medical Systems, Inc., Palo Alto, and USA) linear accelerator at the Nova Scotia Cancer Centre (NSCC). An anthropomorphic phantom was set on the couch and the couch was set at a longitudinal position of 90.85 cm, a vertical position of 15.00 cm, and a lateral position of 0.00 cm. The gantry and couch were rotated over their full range of motions. A point in a collision zone was recorded for which the couch position and gantry position were such that: (i) the collision avoidance system of the TrueBeam was triggered, or (ii) the gantry was within a 5 cm buffer to either the treatment bed or the anthropomorphic phantom. The CG-coordinates within these zones were forbidden zones for the trajectory path. These collision zones were much less conservative than those found in Yang et al, which occupy almost the entire quadrant of the overlap map.

Figure 15:
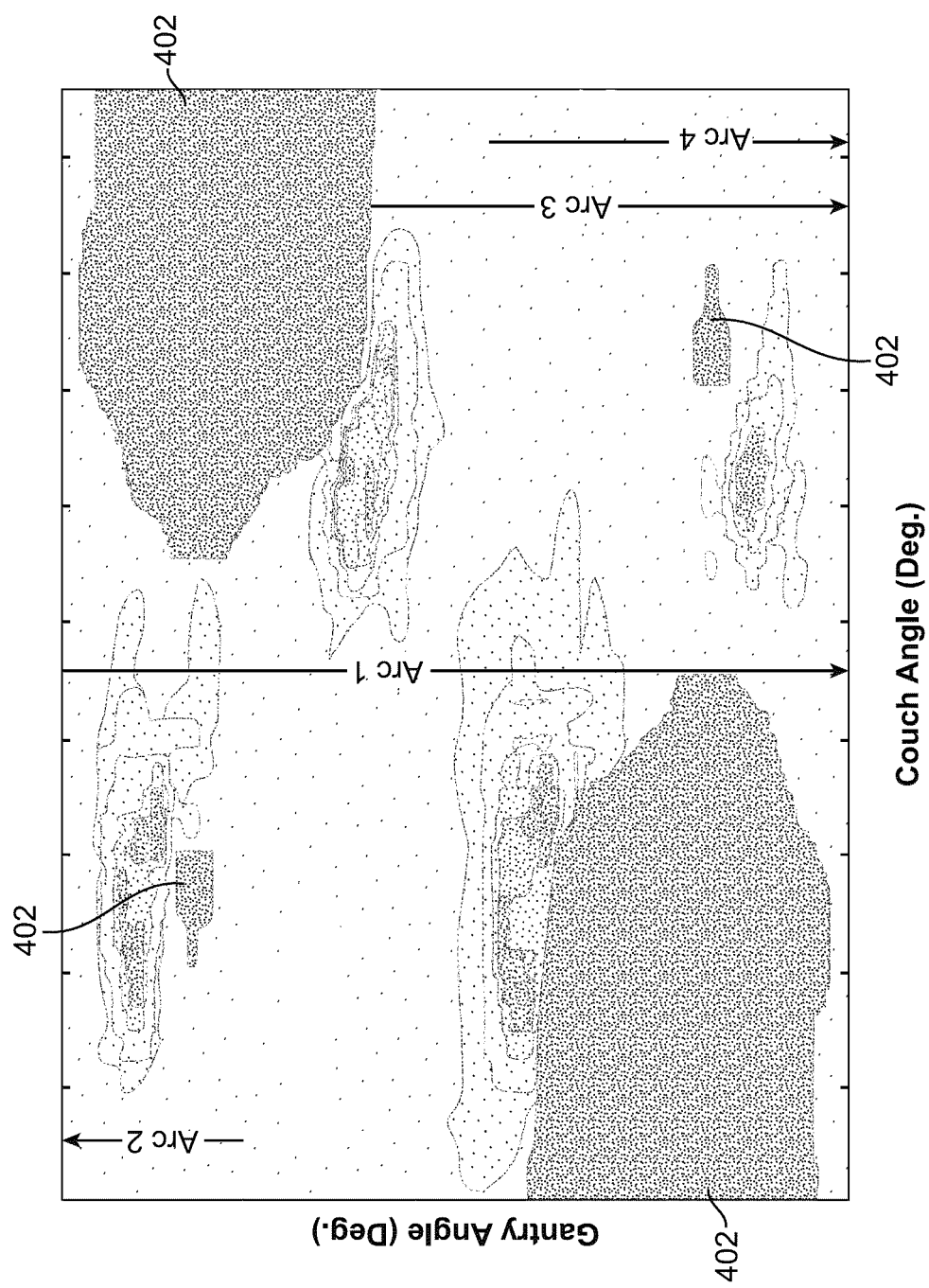
FIG. 15 illustrates a geometric anatomical overlap map for a cranial cancer patient with an optimized fixed-couch trajectory overlaid, according to some embodiments.

Using previously delivered cranial SRT plans treated at the Nova Scotia Cancer Centre (NSCC), we've redesigned the treatment arrangement to find the optimal couch rotation position based on the reduction of overlap between OARs within the patient anatomy and PTV. Maintaining the arc length from the delivered treatment, the couch position was determined based on a cost function analysis of accumulation of overlap score from Equation 4. This principle was first developed to guide non-coplanar, continuous couch trajectories and can have significant dosimetric improvements over guidance of fixed-couch existing treatments. By maintaining the number and length of the arcs from the UAB template, we retain the strengths of this technique and the current treatment paradigm, however we modify the couch rotation angle in order to drastically reduce the risk of dose delivered to the OAR. The arcs shown in FIG. 15 are for a typical patient and are placed on the GOS map in the location which results in the lowest value of overlap. The treatment plans were generated based on these arcs and couch positions and then dosimetrically compared to the conventionally delivered treatment plans.

FIG. 15 illustrates a geometric anatomical overlap map for a cranial cancer patient with an optimized fixed-couch trajectory overlaid, according to some embodiments. FIG. 15 includes multiple collision zones 402.

Urgent Sparing Factor

A new factor has been developed as an addition to the existing cost equation (Equation 5), which was designed to identify radiation therapy couch and gantry positions that limit the involvement of organs-at-risk (OAR) in the beam's aperture. These positions are then used in a trajectory design algorithm which creates couch trajectories in order to perform an effective radiotherapy treatment delivery to the treatment target (PTV), and reduce toxicities to OARs. In the equation featured below, E(c,g) was evaluated for each gantry (g) and patient support rotational angle (c), where $w_i$ is a relative weighting factor for the $i^{th}$ OAR, $L_i(c, g)$ is the overlap area between the PTV and the $i^{th}$ OAR, $A_t(c, g)$ is the area of the $i^{th}$ OAR, and $A_t(c,g)$ is the area of the PTV. We have also established a new factor F, which is a ratio of the value on the depth dose curve for the $i^{th}$ OAR with that of the PTV.

$$E(c, g) = \sum_i w_i \times F(d_1, d_2) \times \left[\frac{L_i(c, g)}{A_t(c, g)} \times \frac{L_i(c, g)}{A_i(c, g)}\right] \quad (5)$$

The new factor aims to address the need for limiting excessive exposure in an OAR in close proximity to the PTV. In some patient geometries, an OAR (most typically the brainstem) is at risk of receiving high dose on the edge closest to the PTV. This factor is included to increase the priority of sparing that outer edge of the OAR when designing a trajectory. By taking advantage of the anatomical arrangement of the PTV and the OAR in need of further sparing, the factor promotes the use of trajectories which are orthogonal to the vector joining the two structures.

Figure 16:
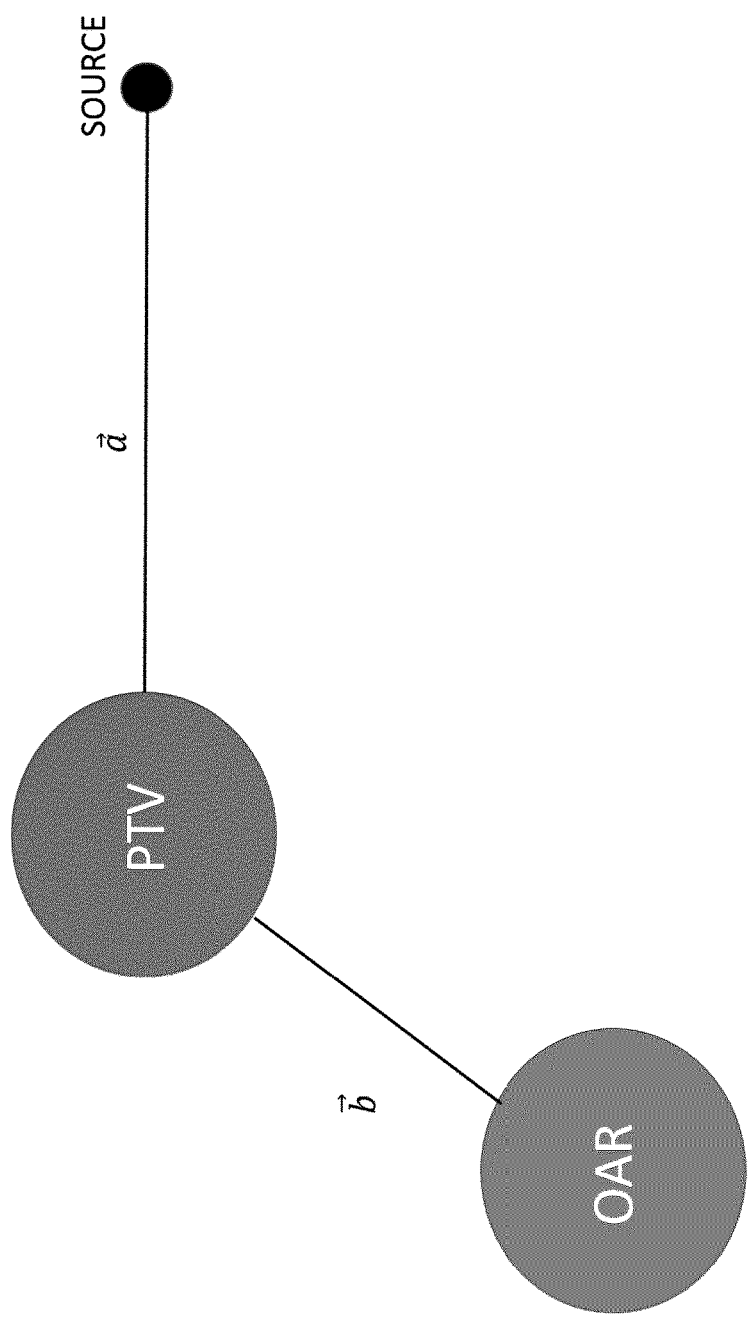
FIG. 16 defines the vectors used in the calculation of the angle used in the urgent sparing factor, according to some embodiments.

When this factor is measured for any OAR, a 3D vector is drawn that joins the two nearest points of the OAR and the PTV. A separate 3D vector is then established for each couch rotation and gantry rotation position which joins the source of radiation to the isocentre. The angle ($\alpha$) between these two 3D vectors is then computed by adding 90 degrees ($\pi/2$ radians) to the arctangent between the plane to which the vector joining source and isocentre is normal, and the vector joining the OAR and PTV at their nearest points. This establishes the angle ($\alpha$) between two three dimensional vectors measured by the shortest circle path between them, and ensures that the angle found lies between 0 and 180 degrees (0 and $\pi$ radians). FIG. 16 displays a geometrical representation of the variables in the calculation of this value. In order to compute this for all angles, it can be understood that with each repositioning of the couch and gantry, these vectors change their 3-dimensional position, the angle $\alpha$ is calculated by:

$$\alpha = \tan^{-1}\left(\frac{\|\vec{a} \times \vec{b}\|}{\vec{a} \cdot \vec{b}}\right)$$

FIG. 16 defines the vectors used in the calculation of the angle used in the urgent sparing factor, according to some embodiments.

Now that this angle $\alpha$ has been established, we want to promote the use of couch and gantry coordinates which force those two vectors to be orthogonal, or $\alpha$ to approach 90 degrees ($\pi/2$ radians). As such we compute the cosine of the angle drawn by the two vectors and add that value to the output of Equation 5. This aligns with the computation of overlap as a geometric overlap corresponds to $\alpha$ at 0 or 180 degrees (0 and $\pi$ radians) or cos $\alpha$=1, which gives a maximum value to E(c,g). See Equation 6 for the full implementation of the overlap metric:

$$E(c, g) = \sum_i \frac{1}{D_{tol_i}} \times \frac{PDD(d_1)}{PDD(d_2)} \times \left[\frac{L_i(c, g)}{A_t(c, g)} \times \frac{L_i(c, g)}{A_i(c, g)}\right] + \cos\left(\tan^{-1}\left(\frac{\|\vec{a} \times \vec{b}\|}{\vec{a} \cdot \vec{b}}\right)\right) \quad (6)$$

Results

Figure 17:
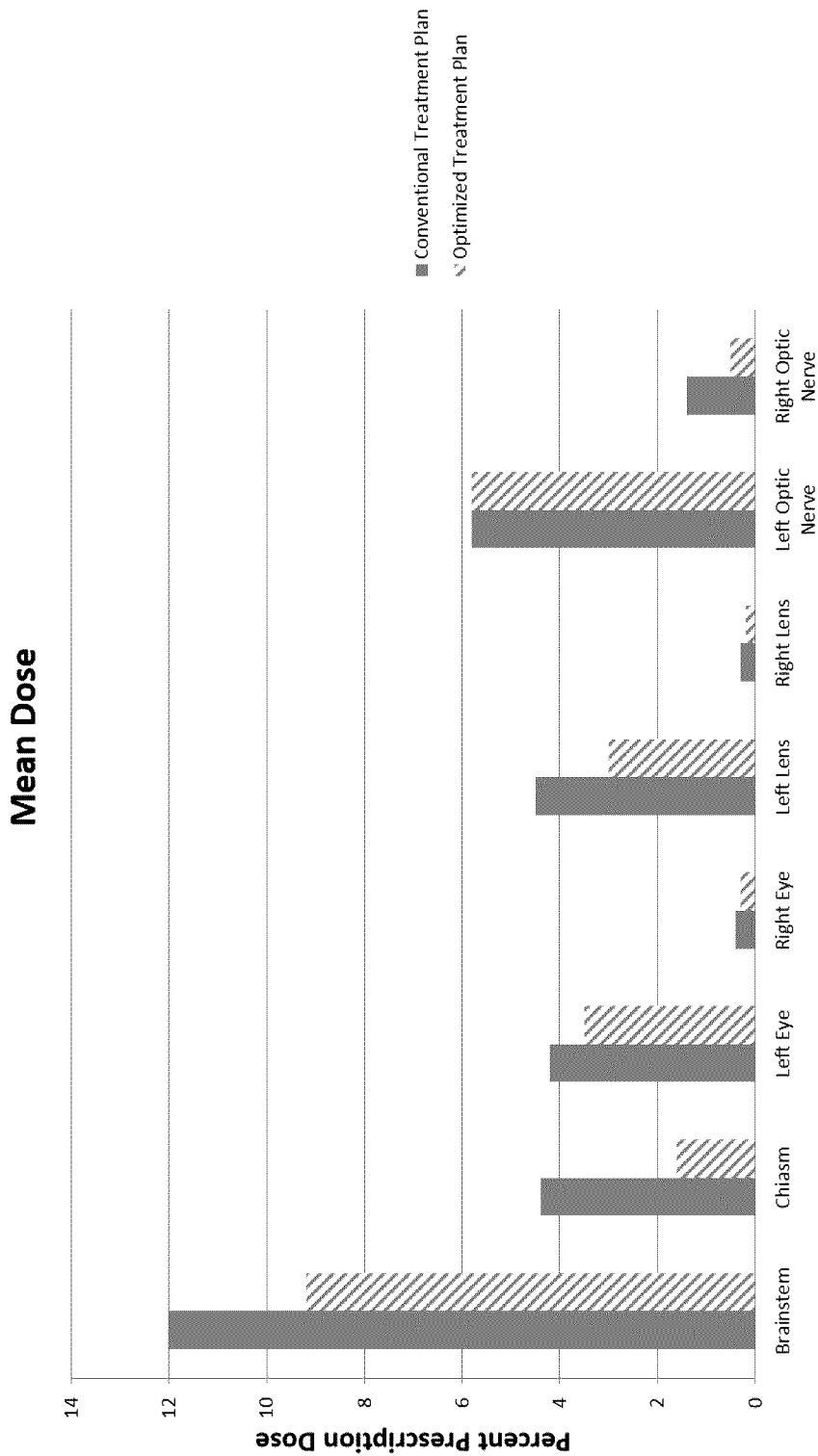
FIG. 17 shows mean dose results for OARs a single patient, according to some embodiments.
Figure 18:
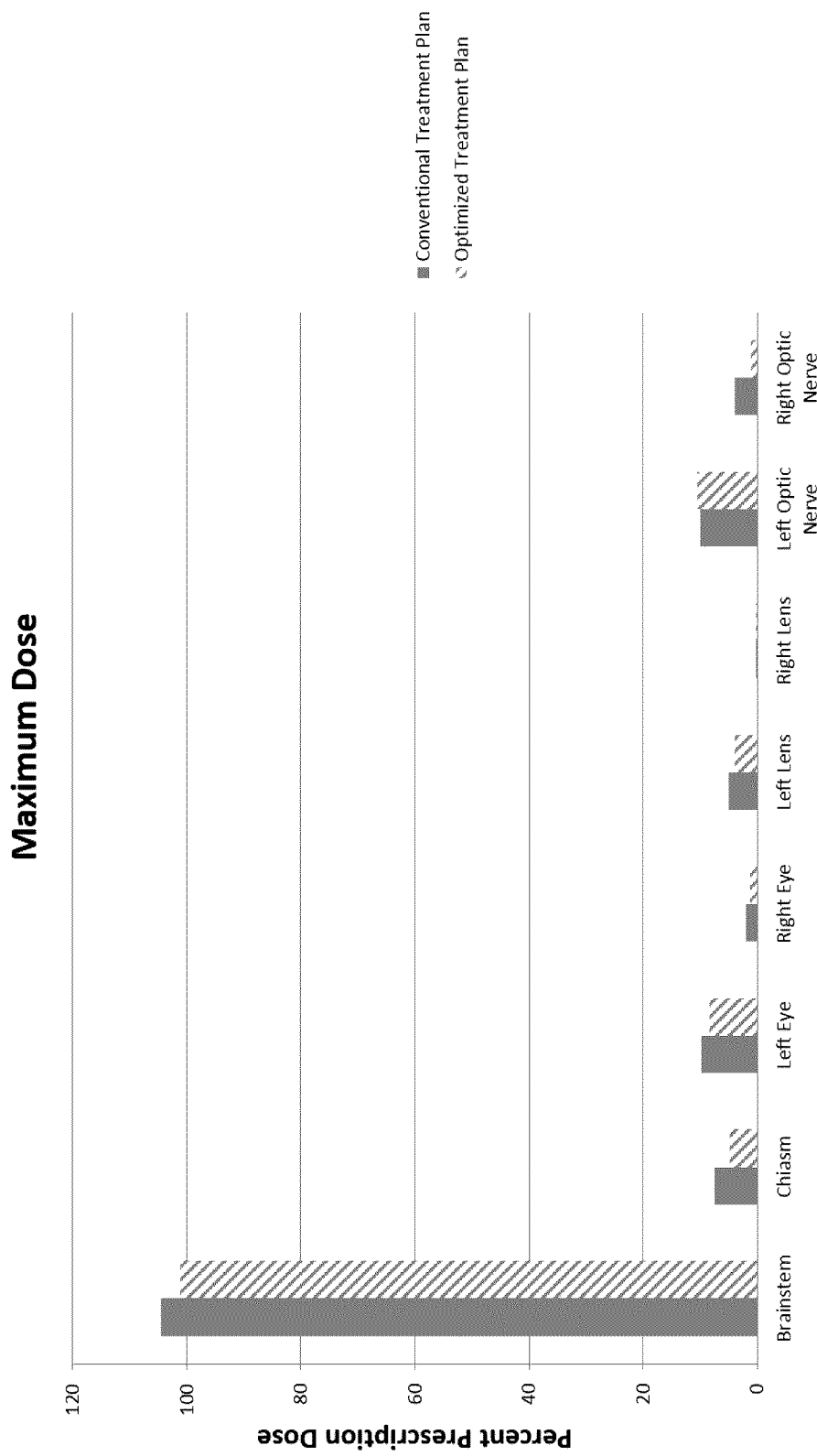
FIG. 18 illustrates maximum dose results for OARs from single patient, according to some embodiments.
Figure 19:
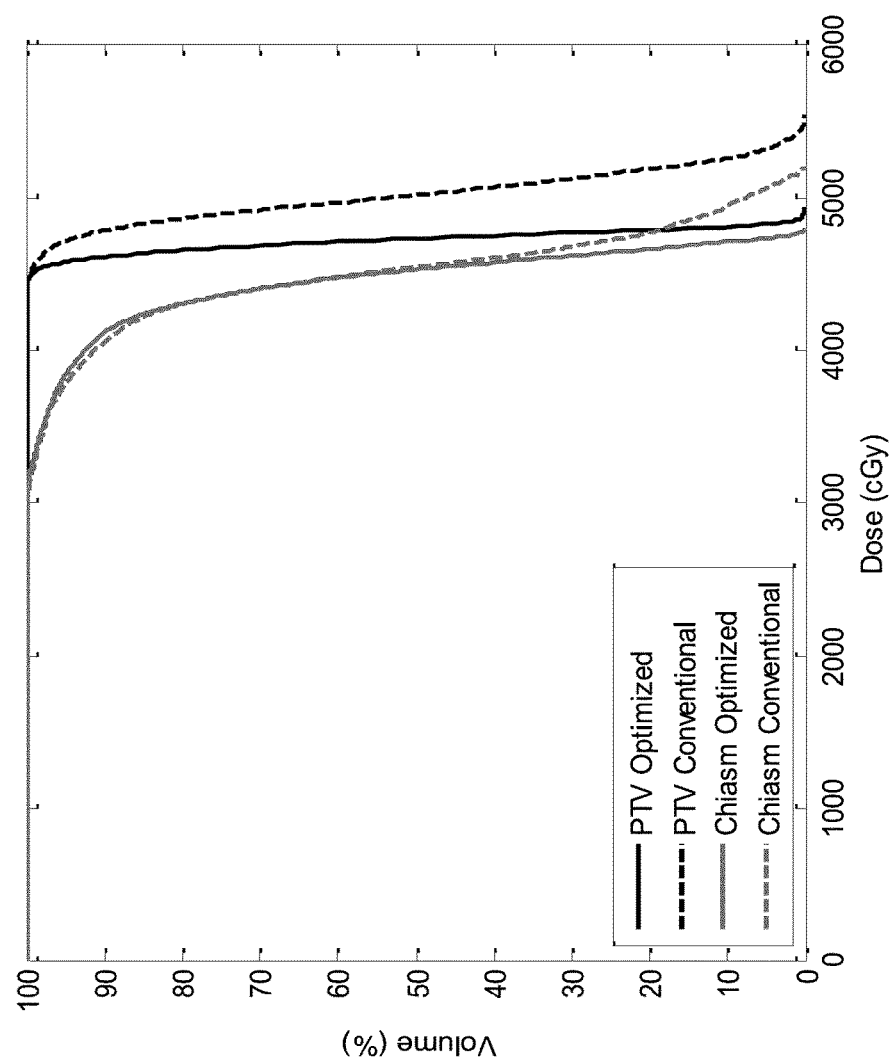
FIG. 19 shows dose volume histograms (DVHs) of the PTV and the Chiasm for an acoustic neuroma patient, according to some embodiments.
Figure 20:
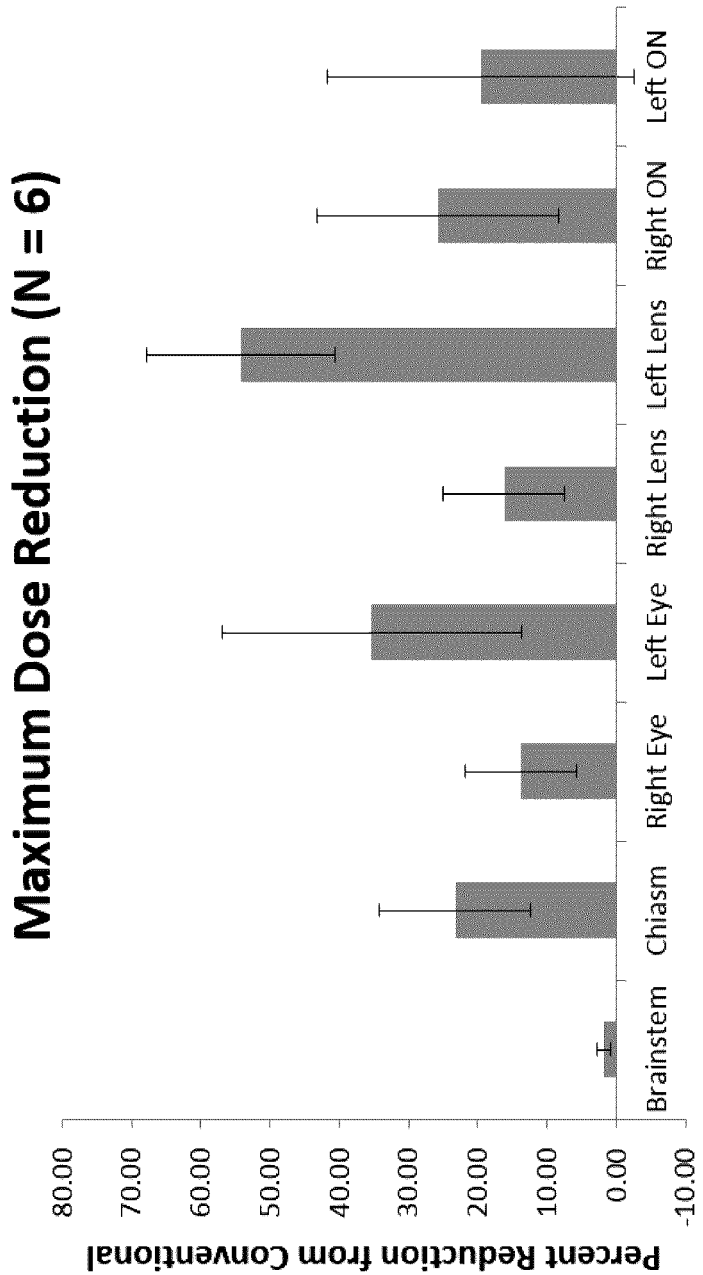
FIG. 20 illustrates averaged percent reduction of maximum dose for each OAR (N=6), according to some embodiments.
Figure 21:
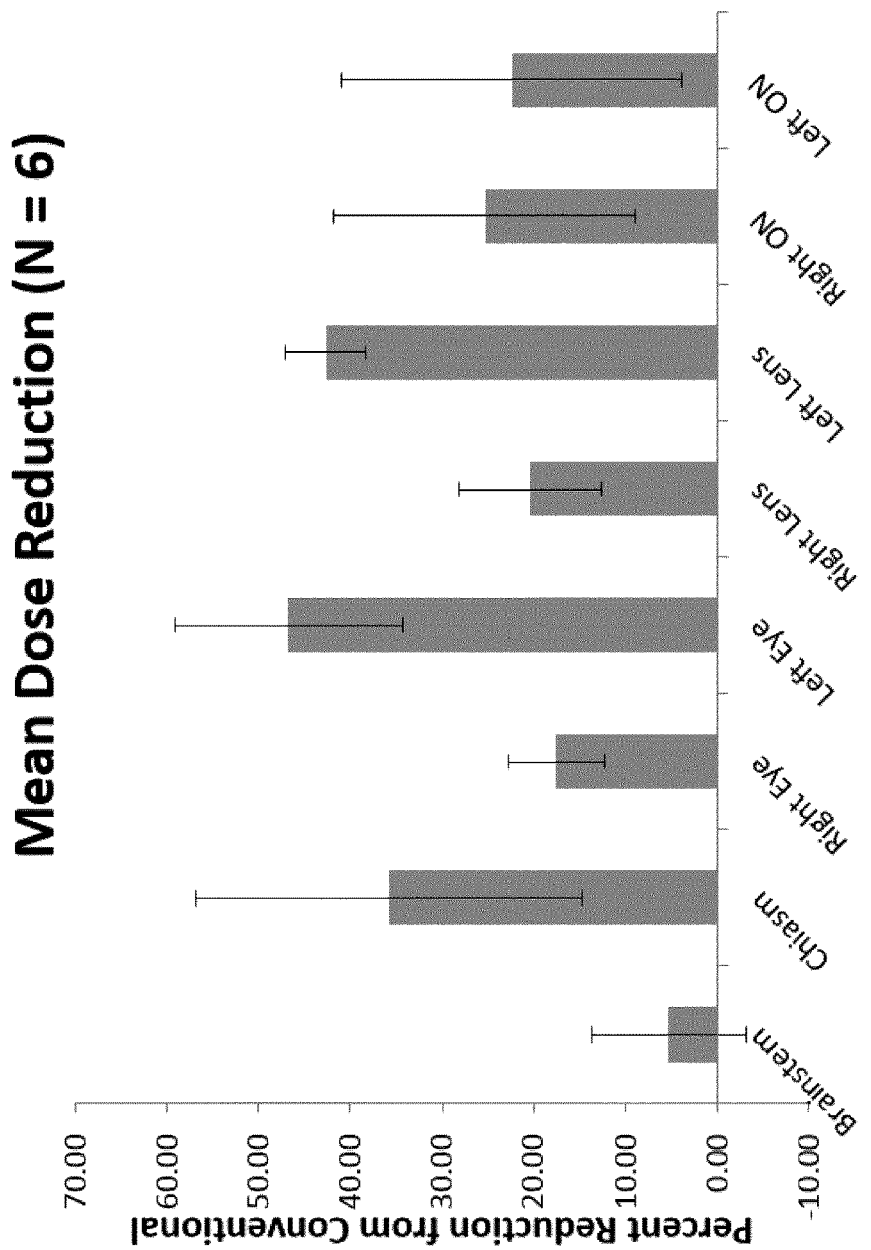
FIG. 21 shows averaged percent reduction of mean dose for each OAR (N=6), according to some embodiments.

The optimization was performed on six cranial cancer patient plans with acoustic neuromas, and resulted in a maximum dose reduction to the OARs of 35.48%±5.38% and a mean dose reduction to the OARs of 36.60%±4.68% (N=6) when compared to conventional trajectory plans. FIGS. 17 and 18 feature the dosimetric mean and maximum results, respectively, for a single patient. FIG. 19 is a plot of the dose volume histograms (DVHs) of the PTV and the optic chiasm for the same patient. FIGS. 20 and 21 show the maximum and mean percent dose reduction, respectively, for all patients examined and each OAR in terms of initial plan doses. These techniques are implementable immediately on any machine, without the need for licenses for advance technologies.

FIG. 17 shows mean dose results for OARs from a single patient.

FIG. 18 illustrates maximum dose results for OARs from a single patient.

FIG. 19 shows dose volume histograms (DVHs) of the PTV and the Chiasm for an acoustic neuroma patient (same patient as FIGS. 17 and 18)

FIG. 20 illustrates averaged percent reduction of maximum dose for each OAR (N=6).

FIG. 21 shows averaged percent reduction of mean dose for each OAR (N=6).

Conclusion

This variation of the existing delivery techniques with guidance from a PTV-OAR overlap cost-function analysis technique yields significant dosimetric improvements, with no increase to delivery or planning time.

The creation of radiotherapy trajectories based on the minimization of overlap between OARs and PTV is an effective means to increase dose sparing in the majority of cranial cancer treatments. In a test-patient population study of six acoustic neuroma cranial SRT patients, the average mean dose reduction to OARs was approximately 35% and the average maximum dose reduction to OARs was approximately 37% of the initial dose given in the treatment of these patients. A reduction of dose to each OAR upon utilization of this trajectory optimization technique was seen, with substantial reduction for the OARs. To measure the effectiveness of optimized plan on treating the target, we've used two indices: the homogeneity index ([6] Oliver, Mike, Jeff Chen, Eugene Wong, Jake Van Dyk, and Francisco Perera. "A Treatment Planning Study Comparing Whole Breast Radiation Therapy against Conformal, IMRT and Tomotherapy for Accelerated Partial Breast Irradiation." Radiotherapy and Oncology: Journal of the European Society for Therapeutic Radiology and Oncology 82, no. 3 (March 2007): 317-23. doi:10.1016/j.radonc.2006.11.021) and the conformity number ([7] van't Tiet, Arie, A D C. A. Mak, Marinus A Moerland, Leo H. Elders, Wiebe van der Zee. "A conformation number to quantify the degree of conformality in brachytherapy and external beam irradiation: Application to the prostate." International Journal of Radiation Oncology Biology Physics 37, no. 3 (Feb. 1, 1997): 731-6. doi: 10.1016/50360-3016(96)00601-3). Dose homogeneity within the PTV and conformity of prescription isodose to the PTV was maintained in the optimized plans when compared to the conventional delivered treatment plans. The dosimetric coverage of the PTV changed very little upon optimization.

The results illustrated indicate substantial advancements to a novel delivery technique.

Anatomically Guided Site-Specific Trajectory Class Solution: Acoustic Neuromas

In addition to defining algorithms for identifying optimal trajectories for dynamic simultaneous coordinated motion between couch and gantry and fixed-couch positioning in cranial stereotactic treatments on a patient specific level, the application of these algorithms can provide a site-specific trajectory class solution. For example, the application of these algorithms on patients with previously designed conventional treatments have illustrated that the patient-specific design of radiotherapy trajectories show significant improvements in dose reduction to sensitive organs without compromising the delivery of prescription dose to the target. This patient-specific approach requires additional optimization in the planning procedure when compared to conventional cranial stereotactic treatments, which have a template trajectory for all cranial cases. While this optimization is minimal in terms of planning time, a site specific class solution would remove this optimization requirement, and would provide a middle-ground between a general cranial trajectory and patient specific treatment. This works aims to define the first of these site specific class solutions for acoustic neuroma patients.

Fifteen anonymized acoustic neuroma patients were used to define the model for this class solution. All patients were analyzed using our overlap analysis methods previously discussed in our dynamic couch algorithm publication and updated in the fixed couch manuscript. In order to generate a geometrical map to represent all patients used in this testing, a maximum intensity projection (MIP) was generated. First, all fifteen maps were read from these acoustic neuroma patients with different relative relationships between target volume and surrounding anatomy, and were identically normalized so that their relative values could be compared. Each pixel within the map was then generated by finding the maximum value for that pixel in all patients. This was conducted so that all patients would have significant weighting in the definition of the trajectory, regardless of their similarity to the rest of the maps in the patient database.

Using the MIP, the conventional cranial stereotactic UAB template was applied and optimized for couch position. The score along each of the arcs in this trajectory was then plotted against gantry angle to identify the largest contributors to score within this trajectory. The mean score value across all arcs was then defined and used as a threshold to remove high scoring portions of the trajectory. If a portion of one of the treatment arcs was above the mean score value, it was removed from the trajectory, leaving only the portions of the trajectories found under the mean score value. The discontinuous sub-arcs that were defined by removal of all points above the mean line are then connected internally so that they are now continuous arcs with the start and stop angle modified when compared to the previously used template. These now can be again optimized for couch rotation, as the arc length has changed since initial calculation.

The removal of portions of the treatment trajectory is the first departure from the gantry angles defined in the UAB template. This is due to the high value of overlap within some portions of these gantry angles for acoustic neuroma patients. As such, we are now optimizing both the couch rotation positions, and the gantry start and stop angle for these treatment trajectories.

Mutual Information Scoring of Geometric Overlap Maps for Knowledge-Based Radiotherapy Planning The GOS overlap maps contain a wealth of information about the anatomical positioning of the patient. This representation is a measure of the three-dimensional arrangement of complex information and can be used as a reference for the current scenario of a patient. Using previously measured GOS maps from a patient population, the radiotherapy plan characteristics, and the outcome of the patient plan, a matching process can be conducted to find the most similar example of a case for a newly scanned patient treatment. Small adjustments to a trajectory can then be made from previously mentioned algorithms to create an automated and patient-specific treatment plan.

Using a mutual information algorithm, the closest GOS map in common with that being scanned can be found and the treatment from this match can then be directly applied to the patient plan. This algorithm calculates the individual entropy of each image, followed by the joint entropy, and then finally calculates the mutual information (MI) value to be used as the metric for an effective match. This algorithm is an extremely quick and efficient way to establish similarities between patient plans.

Purpose: The utilization of mutual information between patient-specific two dimensional overlap maps in order to identify and quantify the similarity in anatomical characteristics in radiotherapy patients.

Methods: Patient-specific anatomical information of cranial, head and neck, and prostate radiotherapy patients were used to quantify the geometric overlap between target volumes and organs-at-risk (OARs) based on their two-dimensional projection from source to a plane at isocenter as a function of gantry and couch angle. QUANTEC and Hall et al dose constraints were then used as weighting factors for the OARs to generate a map of couch-gantry coordinate space indicating degree of overlap at each point in space. Additional factors, including relative tissue depth of structures and couch-gantry collision space for a Varian TrueBeam linac, were used in the creation of two-dimensional maps. The refinement of these geometric maps through previous research at Dalhousie creates an elegant depiction of the 3D complex relationship of anatomical structures surrounding the tumor and simplifies it into a 2D projection. Using a mutual information as the metric, fifty anatomical overlap maps were compared for similarity from a database of previously treated patients.

Results: The mutual information algorithm is successfully able to match to a similar patient anatomy, sensitive to adjustments of <0.50 millimeters. Both affine transformations in translation and dimensional scaling of nearby OARs resulted in substantial decreases in mutual information scoring with relation to the reference patient.

Conclusions: Using the mutual information algorithm, a database of patients can be effectively searched for similarity to a reference patient without any need for congruent nomenclature of structures. Patient planning factors and treatment plan trajectories can be connected to correlate patients quickly and with sub-millimeter anatomical precision.

Figure 22:
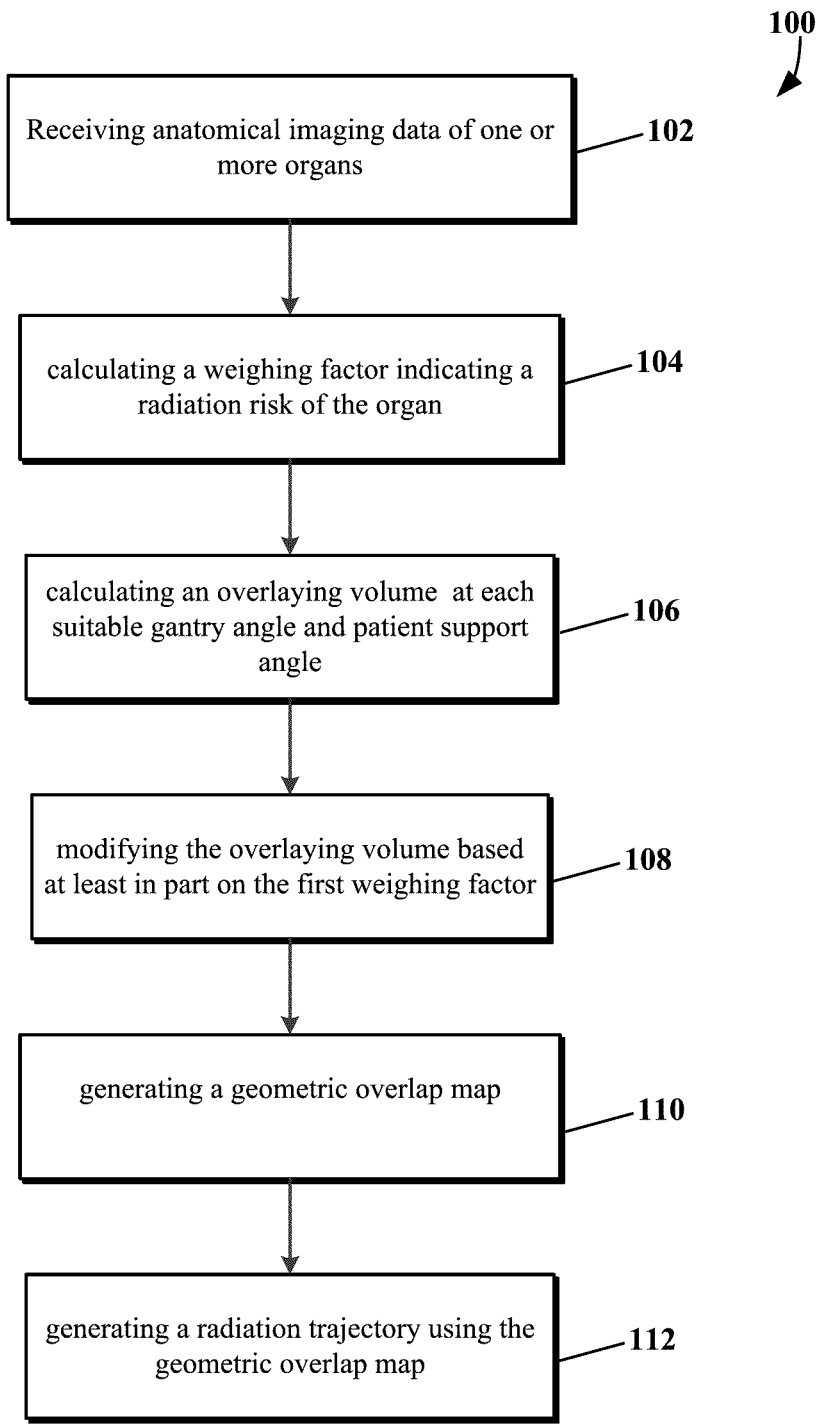
FIG. 22 is an example flow diagram for the automatic trajectory generation system, according to some embodiments.

FIG. 22 is an example flow diagram for the automatic trajectory generation system, according to some embodiments. It should be understood that there can be additional, fewer, or alternative steps performed in similar or alternative orders, or in parallel, within the scope of the various embodiments unless otherwise stated.

At step 102, a processing device can receive anatomical imaging data of one or more organs and a target volume. According to some embodiments, anatomical image data can be a patient's computed tomography (CT) data. According to some embodiments, anatomical image data can be positron emission tomography (PET) data, magnetic resonance imaging (MRI) data, 3D rotational angiography (3DRA) data, or any digital image data that can be helpful for the imaging purpose as described herein.

At step 104, a processing device can calculate a weighting factor associated with each of the one or more organs, the weighting factor indicating a risk of exposing the organ along a radiation path coincident with the target volume. The weighting factor can be a foreground/background weighting factor F. According to some embodiments, this weighting factor (F) can provide further insight to the special conditions of the patient anatomical arrangement, allowing for an accurate trajectory generation. According to some embodiments, the weighting factor (F) can be initially set to an arbitrary value of $1/10$ for an OAR in the foreground of an overlap. This arbitrary value can be further modified based on the percent depth dose curve (PDD).

At step 106, a processing device can calculate an overlapping volume for each of the one or more organs at each suitable gantry angle and each suitable patient support angle. According to some embodiments, each OAR has an overlapping volume corresponding to an overlap area between the OAR and the target volume at each suitable gantry angle and each suitable patient support angle.

At step 108, a device can modify the overlapping volume of each of the one or more organs based at least in part on the first weighting factor associated with each of the one or more organs. According to some embodiments, the modifying can be additionally based on another weighting factor, e.g. radiation sensitivity factor indicating a radiation dose limitation of each of the one or more organs.

At step 110, a processing device can generate a geometric overlap map for the one or more organs by summing the modified overlapping volume of each of the one or more organs.

At step 112, a processing device can generate a radiation trajectory using the geometric overlap map. According to some embodiments, the radiation trajectory can comprise a range of gantry angles suitable for a fixed patient support angles.

Figure 23:
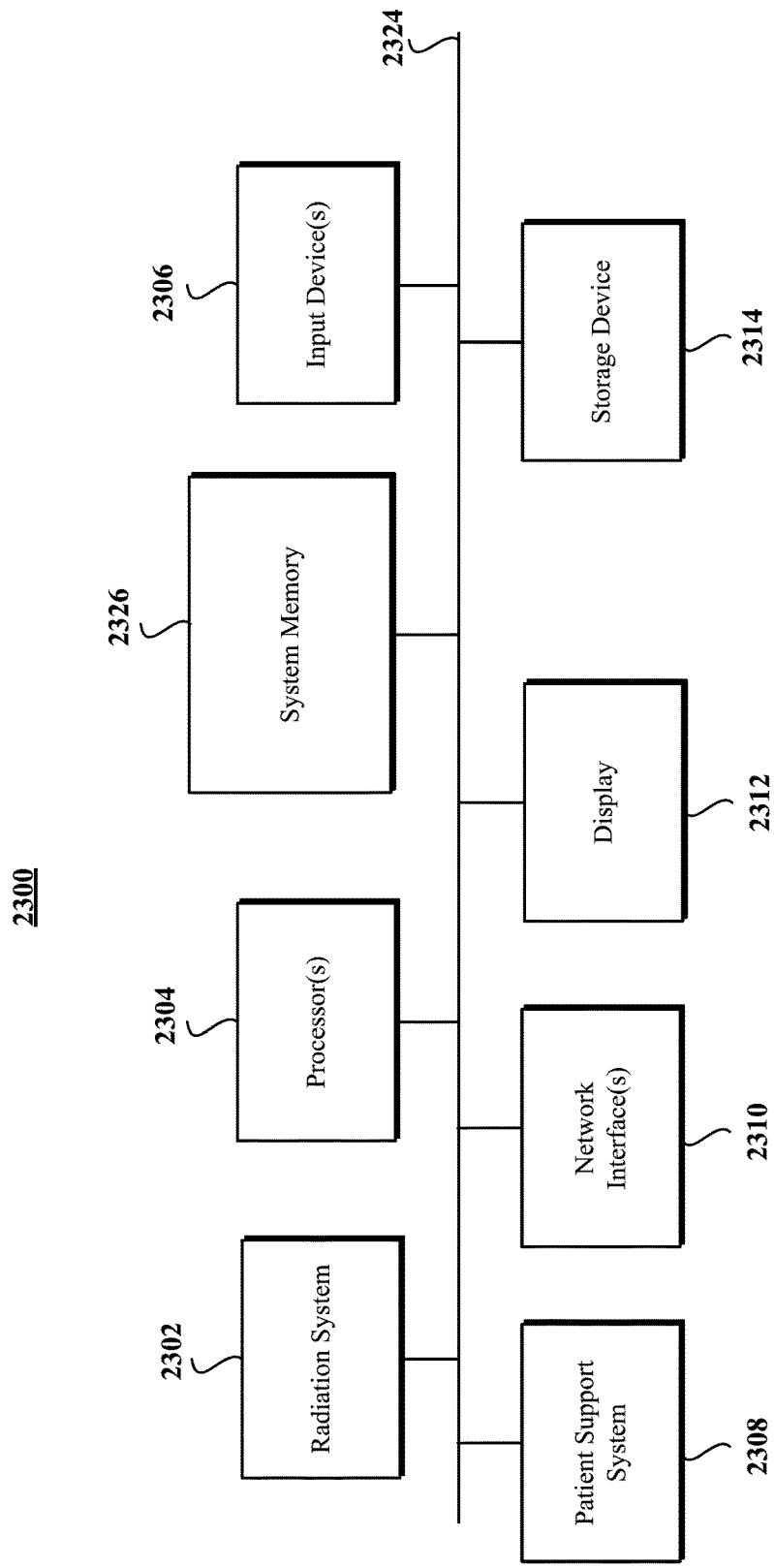
FIG. 23 illustrates an example system architecture 2300 for implementing the systems and processes of FIGS. 1-22.

FIG. 23 illustrates an example system architecture 2300 for implementing the systems and processes of FIGS. 1-9, 12, 13, 15, 16, and 22. Computing platform 2300 includes a bus 2324 which interconnects subsystems and devices, such as: radiation system 2302, processor 2304, storage device 2314, system memory 2326, a network interface(s) 2310, and patient support system 2308. Processor 2304 can be implemented with one or more central processing units ("CPUs"), such as those manufactured by Intel® Corporation—or one or more virtual processors—as well as any combination of CPUs and virtual processors. Computing platform 2300 exchanges data representing inputs and outputs via input-and-output devices input devices 2306 and display 2312, including, but not limited to: keyboards, mice, audio inputs (e.g., speech-to-text devices), user interfaces, displays, monitors, cursors, touch-sensitive displays, LCD or LED displays, and other I/O-related devices.

According to some examples, computing architecture 2300 performs specific operations by processor 2304, executing one or more sequences of one or more instructions stored in system memory 2326. Computing platform 2300 can be implemented as a server device or client device in a client-server arrangement, peer-to-peer arrangement, or as any mobile computing device, including smart phones and the like. Such instructions or data may be read into system memory 2326 from another computer readable medium, such as storage device 1414. In some examples, hard-wired circuitry may be used in place of or in combination with software instructions for implementation. Instructions may be embedded in software or firmware. The term "computer readable medium" refers to any tangible medium that participates in providing instructions to processor 2304 for execution. Such a medium may take many forms, including, but not limited to, non-volatile media and volatile media. Non-volatile media includes, for example, optical or magnetic disks and the like. Volatile media includes dynamic memory, such as system memory 2326.

Common forms of computer readable media includes, for example: floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, or any other medium from which a computer can read. Instructions may further be transmitted or received using a transmission medium. The term "transmission medium" may include any tangible or intangible medium that is capable of storing, encoding, or carrying instructions for execution by the machine, and includes digital or analog communications signals or other intangible medium to facilitate communication of such instructions. Transmission media includes coaxial cables, copper wire, and fiber optics, including wires that comprise bus 2324 for transmitting a computer data signal.

In the example shown, system memory 2326 can include various modules that include executable instructions to implement functionalities described herein. In the example shown, system memory 2326 includes a log manager, a log buffer, or a log repository—each can be configured to provide one or more functions described herein.

Although the foregoing examples have been described in some detail for purposes of clarity of understanding, the above-described inventive techniques are not limited to the details provided. There are many alternative ways of implementing the above-described invention techniques. The disclosed examples are illustrative and not restrictive.

What is claimed is:

1. A non-transitory computer-readable storage medium including instructions that, when executed by at least one processor of a computing device, cause the computing device to:
receive anatomical imaging data of one or more organs-at-risk and a target volume;
determine a two-dimensional, radiation-beam's-eye-view (BEV) centered on the target volume for each of a plurality of gantry positions;
for each BEV for the plurality of gantry positions, calculating a foreground/background weighting factor, the foreground/background weighting factor indicating a risk of exposing a respective organ-at-risk within the BEV as a function of a relative position of the respective organ-at-risk with respect to the target volume and the radiation source; and
determine a preferred gantry position from the plurality of gantry positions by:
calculating a respective overlapping volume for the one or more organs-at-risk for each BEV for the plurality of gantry positions multiplied by the foreground/background weighting factor.

2. The non-transitory computer readable storage medium of claim 1, further comprising instructions that cause the computing device to:
determine that an organ is within a predetermined distance to the target volume; and
calculate an urgent sparing factor associated with the organ for each BEV, the urgent sparing factor based on a cosine of an angle between a line coincident with the BEV and a vector connecting the organ-at-risk and the target volume, wherein the urgent sparing factor is included in the calculating to determine the preferred gantry position.

3. The non-transitory computer readable storage medium of claim 1, wherein determining the BEV centered on the target volume is for each of a plurality of patient support positions.

4. The non-transitory computer readable storage medium of claim 1, wherein determining the BEV centered on the target volume is for each combination of a plurality of patient support positions and the plurality of gantry positions.

5. The non-transitory computer readable storage medium of claim 1, wherein the foreground/background weighting factor is determined based on a ratio of the percent depth dose values of the organ-at-risk to the target volume.

6. The non-transitory computer readable storage medium of claim 1, wherein the respective overlapping volume is associated with an overlap area between the each of the one or more organs-at-risk and the target volume as viewed from the BEV.

7. The non-transitory computer readable storage medium of claim 1, wherein calculating the respective overlapping volume for the one or more organs-at-risk for each BEV is further at least based on a respective radiation sensitivity weighting factor indicating a radiation dose limitation of each of the one or more organs-at-risk.

8. The non-transitory computer readable storage medium of claim 1, wherein the anatomical imaging data comprises at least one of computed tomography (CT) data, positron emission tomography (PET) data, magnetic resonance imaging (MRI) data, or 3D rotational angiography (3DRA) data.

9. The non-transitory computer readable storage medium of claim 1, further comprising instructions that cause the computing device to:
generate a geometric overlap map for the one or more organs-at-risk from the respective overlapping volume for the one or more organs-at-risk for each BEV; and
generate a radiation trajectory using the geometric overlap map.

10. The non-transitory computer readable storage medium of claim 9, wherein the radiation trajectory comprises a range of gantry angles suitable for a fixed patient support angle.

11. The non-transitory computer readable storage medium of claim 9, wherein the radiation trajectory comprises a range of patient support angles suitable for a fixed gantry angle.

12. The non-transitory computer readable storage medium of claim 9, wherein the radiation trajectory comprises a range of gantry angles in correspondence to a range of patient support angles.

13. The non-transitory computer readable storage medium of claim 1, further comprising instructions that, when executed by the at least one processor of the computing device, cause the computing device to:
determine a maximum intensity projection based on geometric overlap maps generated by anatomical imaging data associated with a plurality of patients; and
generate a template geometrical map associated with the plurality of patients.

14. A system for determining a trajectory of a radiation source in radiotherapy, comprising:
a radiation source associated with a gantry angle;
a patient support system associated with a patient support angle;
one or more computer systems configured to:
receive anatomical imaging data of one or more organs-at-risk and a target volume;
determining a two-dimensional, radiation-beam's-eye-view (BEV) centered on a target volume for each of a plurality of gantry positions;
calculate a respective foreground/background weighting factor for each BEV of the plurality of gantry positions, the foreground/background weighting factor indicating a risk of exposing a respective organ-at-risk within the BEV as a function of the relative position of the organ-at-risk with respect to the target volume and the radiation source;
calculate a respective overlapping volume for the each of the one or more organs-at-risk at each suitable gantry angle and each suitable patient support angle;
modify the respective overlapping volume of the each of the one or more organs-at-risk based at least in part on the respective foreground/background weighting factor and a radiation sensitivity weighting factor associated with each of the one or more organs-at-risk;
generate a geometric overlap map for the one or more organs-at-risk by summing the modified overlapping volume of the each of the one or more organs-at-risk; and
generate a radiation trajectory using the geometric overlap map.

15. The system of claim 14, further configured to:
determine that an organ is within a predetermined distance to a target volume or receives a measure of excess dose; and
calculating an urgent sparing factor associated with the organ for each BEV, the urgent sparing factor based on a cosine of an angle between a line coincident with the BEV and a vector connecting the organ and the target volume, wherein the urgent sparing factor is used to modify the respective overlapping volume of the each of the one or more organs-at-risk.

16. The system of claim 14, wherein the anatomical imaging data is associated with a specific patient.

17. The system of claim 14, wherein the respective foreground/background weighting factor is determined based at least in part on respective percent depth dose values of the respective organ-at-risk and the target volume.

18. The system of claim 14, wherein the respective overlapping volume is associated with an overlap area between each of the one or more organs-at-risk and the target volume as viewed from the BEV.

19. The system of claim 14, wherein the radiation sensitivity weighting factor indicates a radiation dose limitation of the each of the one or more organs-at-risk.

20. The system of claim 14, wherein the anatomical imaging data comprises at least one of computed tomography (CT) data, positron emission tomography (PET) data, magnetic resonance imaging (MRI) data, or 3D rotational angiography (3DRA) data.

21. A computer-implemented method for determining a trajectory of a radiation source in radiotherapy, comprising:
receiving anatomical imaging data of one or more organs-at-risk and a target volume;
determining a two-dimensional, radiation-beam's-eye-view (BEV) centered on the target volume for each of a plurality of gantry positions;
for each BEV for the plurality of gantry positions, calculating a foreground/background weighting factor, the foreground/background weighting factor indicating a risk of exposing a respective organ-at-risk within the BEV as a function of a relative position of the respective organ-at-risk with respect to the target volume and the radiation source;
determining a preferred gantry position from the plurality of gantry positions by:
calculating a respective overlapping volume for the one or more organs-at-risk for each BEV for the plurality of gantry positions multiplied by the foreground/background weighting factor;
generating a geometric overlap map for the one or more organs-at-risk from the respective overlapping volume for the one or more organs-at-risk for each BEV; and generating a radiation trajectory using the geometric overlap map.

22. The computer-implemented method of claim 21, wherein calculating the respective overlapping volume is further at least based on a urgent sparing factor associated with each of the one or more organs-at-risk, the urgent sparing factor based on a cosine of an angle between a line coincident with the BEV and a vector connecting the organ-at-risk and the target volume.

23. The computer-implemented method of claim 21, wherein calculating the respective overlapping volume is further at least based on a radiation sensitivity weighting factor associated with each of the one or more organs-at-risk, the radiation sensitivity weighting factor indicating a radiation dose limitation of the each of the one or more organs-at-risk.

24. The computer-implemented method of claim 21, further comprising:

determining a maximum intensity projection based on geometric overlap maps generated by anatomical imaging data associated with a plurality of patients; and generating a template geometrical map associated with the plurality of patients.

25. The computer-implemented method of claim 21, further comprising:

comparing a plurality of geometric overlap maps, each of the plurality of geometric overlap maps associated with a respective patient; and identifying one or more similar anatomical characteristics in the plurality of geometric overlap maps.

26. The computer-implemented method of claim 25, further comprising:

modifying the radiation trajectory based at least in part on the one or more similar anatomical characteristics in the plurality of geometric overlap maps.

* * * * *